United States Patent
Mueller et al.

(10) Patent No.: US 6,908,435 B1
(45) Date of Patent: Jun. 21, 2005

(54) METHOD AND MONITOR FOR ENHANCING ANGIOGENESIS IN THE HEART BY EXERCISE FOLLOW-UP

(75) Inventors: Richard L. Mueller, Byron, CA (US); U. Hiram Chee, Santa Cruz, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 80 days.

(21) Appl. No.: 09/706,583
(22) Filed: Nov. 3, 2000

Related U.S. Application Data

(60) Provisional application No. 60/163,701, filed on Nov. 5, 1999.

(51) Int. Cl.[7] ................................................. A61B 5/02
(52) U.S. Cl. ..................................... 600/500; 600/520
(58) Field of Search ............................... 600/500, 509, 600/510, 520; 607/4–7, 9, 11

(56) References Cited

U.S. PATENT DOCUMENTS

| | | | | |
|---|---|---|---|---|
| 5,244,460 A | * | 9/1993 | Unger et al. ................ | 604/508 |
| 5,421,331 A | * | 6/1995 | Devito et al. ................ | 600/425 |
| 6,473,644 B1 | * | 10/2002 | Terry et al. ..................... | 607/2 |
| 6,524,324 B1 | * | 2/2003 | Mueller et al. ............. | 606/185 |
| 6,748,258 B1 | * | 6/2004 | Mueller et al. ............. | 600/425 |

* cited by examiner

Primary Examiner—Jeffrey R. Jastrzab
Assistant Examiner—Frances P. Oropeza
(74) Attorney, Agent, or Firm—Jones Day

(57) ABSTRACT

Various methods and devices for treating a patient who has lost, or is at risk of losing cardiac function by cardiac ischemia are disclosed. Treatment includes first imaging a patient's heart, or a portion thereof, to identify underperfused regions of cardiac muscle, and a source of oxygenated blood that is proximate to the underperfused region. Between the underperfused regions and the oxygenated blood source, a target area is selected where thermal or mechanical injury is introduced, and optionally reintroduced, to convert initial capillary blush, resulting from the injury.

14 Claims, 14 Drawing Sheets

US 6,908,435 B1

METHOD AND MONITOR FOR ENHANCING ANGIOGENESIS IN THE HEART BY EXERCISE FOLLOW-UP

This application claims priority of U.S. Provisional patent application Ser. No. 60/163,701 filed on Nov. 5, 1999, herein incorporated in its entirety by reference.

FIELD OF THE INVENTION

The present invention relates to methods and devices for treating a patient at risk of loss of cardiac function by cardiac ischemia.

REFERENCES

The following references are cited in this application, either as references pertinent to the Background of the Invention, or to methods or materials described in the Detailed Description of the Invention.

BACKGROUND OF THE INVENTION

Heart disorders are a common cause of death in developed countries. They also impair the quality of life of millions of people and restrict activity by causing pain, breathlessness, fatigue, fainting spells and anxiety. The major cause of heart disease in developed countries is impaired or inadequate blood supply. The coronary arteries may become narrowed due to arteriosclerosis and part of the heart muscle is deprived of oxygen and other nutrients. The resulting ischemia or blockage can lead to angina pectoris, a pain in the chest, arms or jaw due to lack of oxygen to the heart's myocardium, infarction or tissue necrosis in myocardial tissue. Alternatively, and particularly with age, the extent of vascularization of the heart may diminish, leaving the heart undersupplied with oxygen even in the absence of significant arteriosclerosis.

Coronary-artery blockage can be relieved in a number of ways. Drug therapy, including nitrates, beta-blockers, and peripheral vasodilator drugs (to dilate the arteries) or thrombolytic drugs (to dissolve clots) can be very effective. If drug treatment fails, transluminal angioplasty is often indicated the narrowed part of the artery, clogged with atherosclerotic plaque or other deposits, can be stretched apart by passing a balloon to the site and gently inflating it a certain degree. In the event drug therapy is ineffective or angioplasty is too risky (introduction of a balloon in an occluded artery can cause portions of the arteriosclerotic material to become dislodged which may cause a total blockage at a point downstream of the subject occlusion, thereby requiring emergency procedures), the procedure known as coronary artery bypass grafting (CABG) is the most common and successful major heart operation performed, with over 500,000 procedures done annually in America alone. A length of vein is removed from another part of the body. The section of vein is first sewn to the aorta and then sewn onto a coronary artery at a place such that oxygenated blood can flow directly into the heart. CABG typically is performed in an open chest surgical procedure, although recent advances suggest minimally invasive surgery (MIS) techniques may also be used.

Another method of improving myocardial blood supply is called transmyocardial revascularization (TMR), the creation of channels from the epicardial to the endocardial portions of the heart. Initially, the procedure used needles to perform "myocardial acupuncture," and has been experimented with at least as early as the 1930s and used clinically since the 1960s, see Deckelbaum. L. I., Cardiovascular Applications of Laser Technology, *Lasers in Surgery and Medicine* 15:315–341 (1994). This procedure has been likened to transforming the human heart into one resembling that of a reptile. In the reptile heart, perfusion occurs via communicating channels between the left ventricle and the coronary arteries. Frazier, O. H., Myocardial Revascularization with Laser—Preliminary Findings, *Circulation*, 1995; 92 [suppl II:II-58-II-65]. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. The needle technique was not continued because the channels did not remain open, replaced by the use of laser energy to accomplish TMR.

Drug therapies with angiogenic growth factors may expedite and/or augment collateral artery development. To accomplish these needs, drug transfer devices for delivering precise amounts of these drugs can enhance this healing process. Surgeons who deal with minimally invasive surgical techniques, and interventional cardiologists who deal with percutaneous approaches, need devices for drug delivery procedures. The drugs used in modern medical technology are often quite expensive, potentially mixing and/or handling sensitive, and it is a new challenge to make these drugs or other compounds readily available for precise, predetermined delivery during these advanced or other procedures.

SUMMARY OF THE INVENTION

The invention includes, in one aspect, a method of treating a patient suffering from or at risk of suffering from loss of cardiac function by cardiac ischemia. The method is practiced by first imaging the patient's heart, or a portion thereof, to identify (i) an underperfused region of cardiac muscle, (ii) a source of oxygenated blood that is proximate a boundary of the underperfused region, and (iii) a target area that includes the underperfused region boundary and a tissue expanse lying between the oxygenated blood supply and the boundary. A stimulus effective to stimulate angiogenesis in myocardial tissue and form a capillary network from the oxygenated blood supply to the underperfused region is introduced at each of a plurality of sites throughout the target area. Thereafter, the patient is equipped with an exercise monitor that indicates the level and amount of heart exercise effective to stimulate the conversion of capillary blush produced by the introduction of the stimulus to arterioles in the target area.

In another aspect, the invention includes a monitor adapted to be worn by a patient after a surgical procedure and designed to identify heart regions in need of enhanced vascularization, and induce capillary blush in such regions. A sensor monitors the patient heart rate, and a processor calculates the total time that the patient's heart rate is above a selected level, and the total number of days needed to induce transformation of the capillary blush into arterioles, based on the level of exercise being monitored. The information calculated by the processor is displayed on a display device.

The underperfused region is an at risk region of cardiac muscle which is insufficiently perfused to handle heightened activity or is likely to be near term at risk of underperfusion due to the progression of nearby disease and cannot be treated by the full restoration of normal coronary flow.

Usually, patients will enter this treatment regiment by appearing for intermittent angina (intermittent identifies that demand for arterial growth and arterial maturation is not reliably turned on) through drug or exercise stress testing where cardiac reserve appears less than optimal or when a routine treatment such as bypass, angioplasty or stents is unable to restore normalized blood flow, and in the judgment of the cardiologist or surgeon is at risk due to lack of reserve capacity. The imaging step to identify the area at risk and nearby source of oxygenated blood (target) may be carried out by monitoring blood flow in the heart by myocardial perfusion imaging by single-photon emission computed tomography (SPECT), positron-emission tomography (PET), echo-planar imaging, MRI, or angiogram.

The source of oxygenated blood in the method may be one in which arteries less than about 1 mm branch into surrounding arterioles, and in which the arterioles with inner-lumen diameters between about 50–200 microns are plentiful, and the sites are spaced from one another at spacing of between 0.5 to 1 cm. Alternatively, or in addition, the underperfused region may be a myocardial region of either of the patient's ventricles, and the source of oxygenated blood, the interior of the underperfused heart ventricle region. Here the target area includes the region of ventricle endocardium underlying the underperfused region.

The stimulus introduced at each of the target-area sites may be a growth factor, such as basic or acidic fibroblast growth factor-1 (FGF-2, FGF-1), vascular endothelial growth factor (VEGF), platelet-derived growth factor (PDGF), insulin-like growth factor-1 (IGF-1), or combinations of two or more of these growth factors. The growth factor may be introduced in the form of a recombinant protein carried in a pharmaceutically acceptable medium, a vector containing the coding sequence for the growth factor and a control region effective to promote transcription of the coding region in patient myocardial cells, and/or in the form of a myocardial or cardiac myoblast cells which have been transformed with a gene encoding the growth factor. The manner of introducing the growth factor may be by (i) injecting the protein, vector of cells directly into myocardial tissue at each site, (ii) drawing the protein or vector into myocardial tissue at each site by iontophoresis from a reservoir placed against the site, (iii) forming a channel in the myocardium at each site, and placing the protein, vector or cells into the channel, or (iv) bombarding each site with a biolistic particle containing or coated with the protein, vector or cells. For example, an angiogenic stimulus would be used without adjunctive biological triggering when the target area is predetermined at the patient evaluation and diagnosis stage to have sufficient preexisting tissue demand for oxygen in the form of significant angina (Canadian Heart Class 4) or when the physician has predetermined that the patient can exercise post treatment to provide dependable tissue demand for arteriole growth beyond the preexisting patient reserve capacity.

In another general embodiment, the stimulus introduced into the target-area sites is an injury produced by a mechanical, laser, chemical, thermal, or ultrasonic stimulus. This type of stimulus may be additive to the effect of a drug stimulus by turning on the local naturally-occurring angiogenic processes. In the process of adding a biologic trigger a new immediate tissue demand for oxygen is added which can be effectively used where Class 4 Angina is not available and exercise cannot be used due to related concerns. For example, the injury may be produced by a mechanical cutting device effective to produce an annulus of injury about a core of healthy cells. Alternatively, the injury may be produced by introducing into each of the sites, a wire device having a barbed segment, where the method further includes periodically moving the wire devices relative to the heart, to produce a prolonged angiogenic stimulus at the site. In another example the stimulus may include a mechanical injury produced by forming, at selected target sites in the target area, elongate channels in the endocardium of the ventricle to stimulate angiogenic growth from the ventricle to neighboring target regions as described above. The depth and width of the endocardial channels, combined with the blood turbulence produced within the ventricle, is such as to minimize accumulation of blood clot material in the channels. The channels have preferred width and depth dimensions between 1–5 mm. This embodiment of the method may further include imaging the heart to identify (i) as a second source of oxygenated blood, coronary arterioles in the epicardial region of the ventricle overlying the underperfused heart-ventricle region, (ii) as a second target area, the area between the second source of oxygenated blood supply and the underperfused region, and the adjacent boundary of the underperfused region. There is then introduced into the second target area, at selected sites therein, a stimulus effective to stimulate angiogenesis in the target area. Sustained demand can also be created with chemical methods such as acidic injections, with foreign body responses as with mildly toxic implants, and with viral carriers which might be used to facilitate angiogenic gene transfer.

These and other and features of the invention will become more fully apparent when the following detailed description of the invention is read in conjunction with the accompanying drawings.

DETAILED DESCRIPTION OF THE INVENTION

1. Treatment Method

Figure 1:
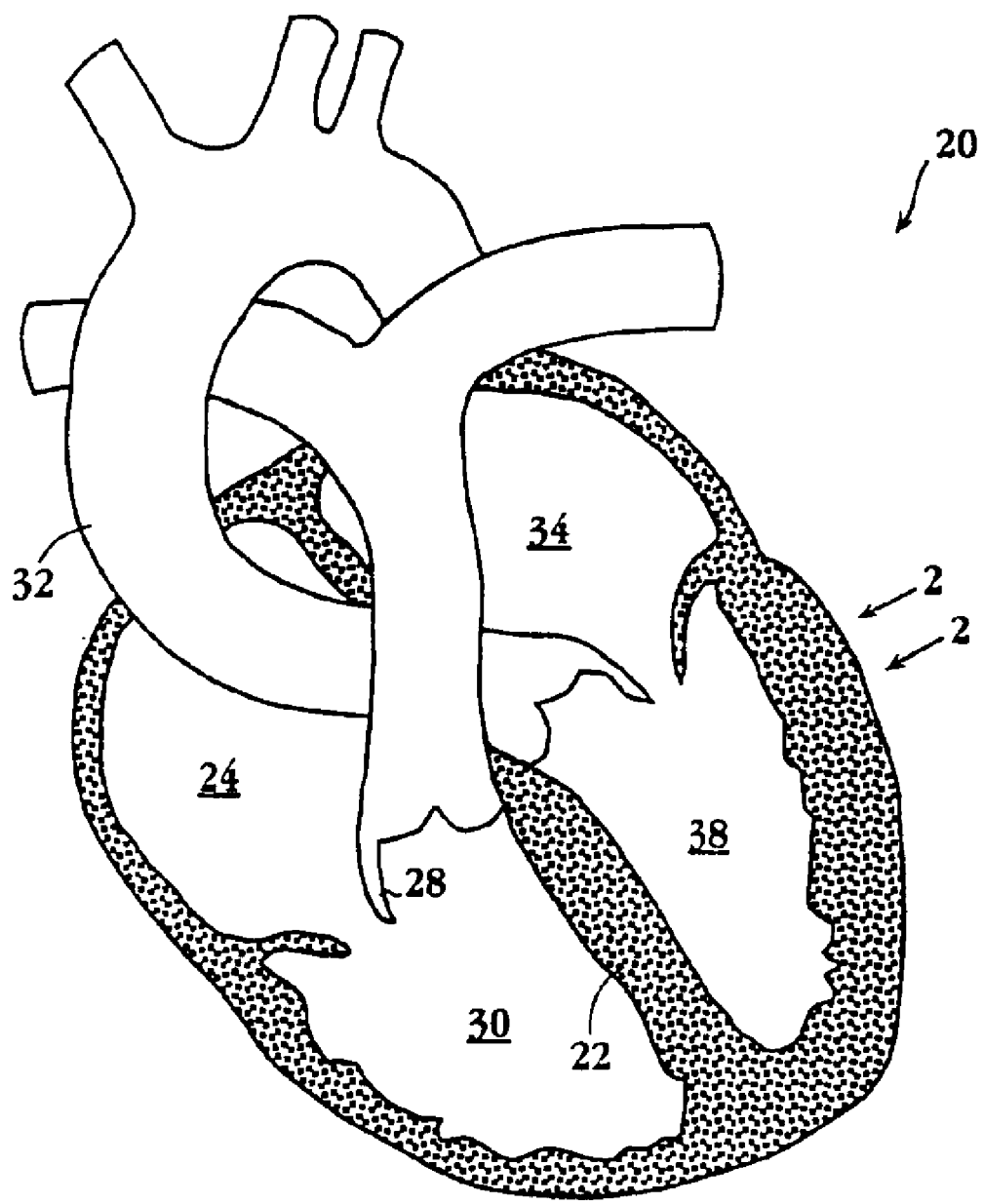
FIG. 1 is a simplified view of a human heart.

FIG. 1 is a simplified view of a human heart 20. The interior of the heart is divided into right and left halves by a thick central muscular wall 22 known as a septum. On the right side, the upper chamber is known as the right atrium, indicated at 24. Deoxygenated blood from the rest of the body arrives in the right atrium via the vena cava, and is pumped across a one-way valve 28 known as the tricuspid valve into the lower right chamber known as the right ventricle, indicated at 30. From there the blood circulates to the lungs through the pulmonary valve via the pulmonary artery where it is oxygenated by circulation through the alveoli of the lungs (not shown). The blood returns via the pulmonary veins to the left atrium, shown at 34 and flows through a second valve, known as the mitral valve, into the left ventricle, indicated at 38, where it is pumped via the aorta 32 to the rest of the body.

Figure 2A:
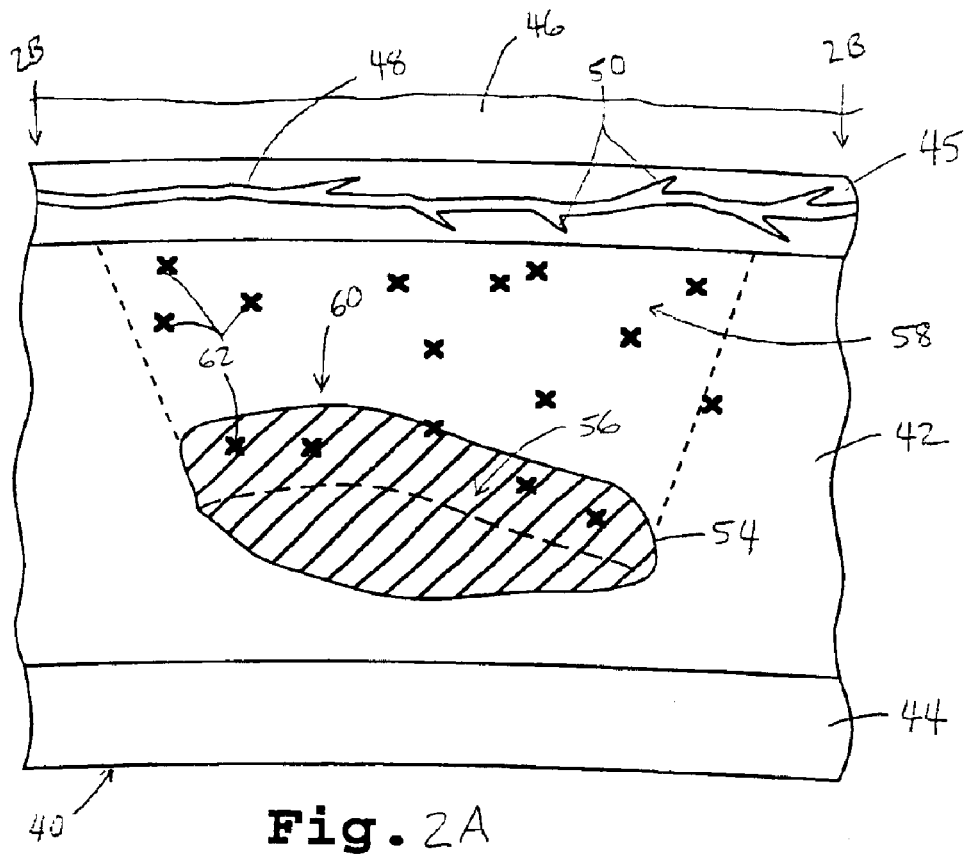
FIGS. 2A and 2B show cross-sectional (2A) and plan (2B) views of a ventricle wail a human heart, in an underperfused region of the wall, and corresponding generally to the region of line 2—2 in FIG. 1.
Figure 2B:
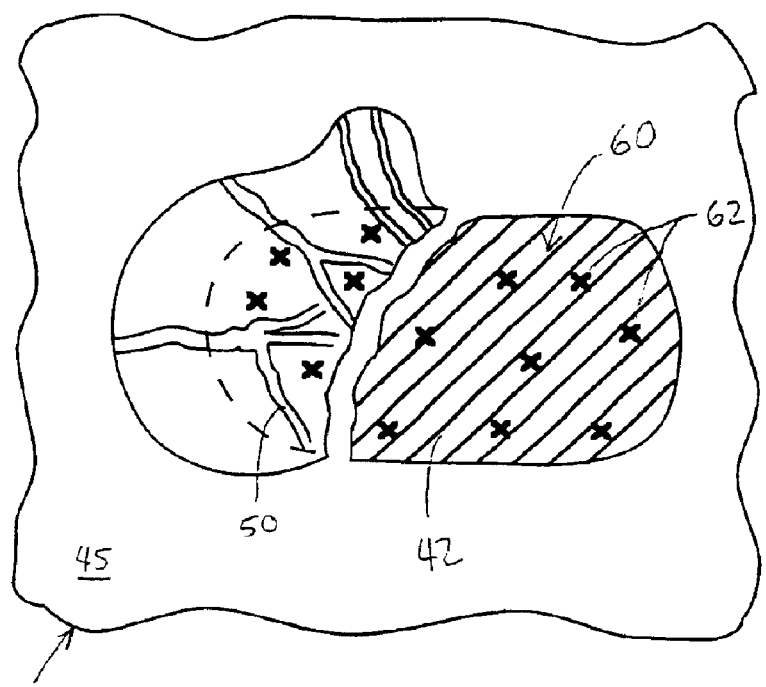

With reference to FIGS. 2A and 2B, which show a wall portion 40 of the heart left ventricle corresponding to view line 2—2 in FIG. 1, much of the heart consists of a special type of muscle called myocardium, indicated at 42. The myocardium requires a constant supply of oxygen and nutrients to allow it to contract and pump blood throughout the vasculature. The inner surfaces of the chambers of the heart are lined with a smooth membrane 44, the endocardium, and the entire heart is enclosed in a tough, membranous bag 46, known as the pericardium or pericardial sac.

Though the heart supplies blood to all other parts of the body, the heart itself has relatively little communication with the oxygenated blood supply. Thus, the two coronary arteries, the left coronary artery and the right coronary artery, arise from the aorta and encircle the heart muscle on either side "like a crown" to supply the heart itself with blood. Coronary arteries are shown at 48 in FIGS. 2A and 2B, and the arterioles branching from these arteries, at 50. The arteries and arterioles are largely confined to the epicardium 45 and adjacent regions of the myocardium. The arterioles, in turn, feed a capillary bed within the three heartwall layers. A venous capillary system in the same layers returns blood from the coronary arteries to the coronary veins, the coronary sinus, and the right atrium.

A. Supply-and-Demand Model

The present invention provides methods and devices for treating a patent at risk of loss of cardiac function by cardiac ischemia. The methods are designed to increase blood flow or circulation from a source of oxygenated blood in the heart to a region that is underperfused—that is, a region that is receiving less oxygenated blood than that optimally required by the heart under a moderate load or stress. As a consequence of this underperfusion, or ischemia, the patient is at risk of, or has already suffered some loss of, cardiac muscle used in normal heart functioning. If the patient at risk has already suffered some loss of heart muscle, the region of lost muscle is referred to as a nonviable muscle, indicative of a cardiac infarction.

In practicing the treatment method, one first images the patient's heart, to a identify (i) an underperfused region of cardiac muscle, (ii) a source of oxygenated blood that is proximate a boundary of the underperfused region, and (iii) a target area that includes the underperfused-region boundary and a tissue expanse lying between the oxygenated blood supply and said boundary. The imaging may also be used to identify (iv) the degree or magnitude of high grade tissue demand for oxygenated blood that is naturally occurring in the underperfused region and based on this assessment if a biological trigger will be added.

The imaging step is illustrated in FIGS. 2A and 2B, illustrating a portion of a heart ventricle wall 40 as described above. The figures show an underperfused region 54 in the myocardium of a ventricle wall. The underperfused region contains at least some viable, but hibernating muscle (i) whose functioning can be improved by increased blood supply to the region, and/or (ii) which is at high risk of suffering future injury due to the advanced state and expected progression of disease (iii) which in the physician's judgment is not ideal for an expected safe full normal blood flow restoration procedure such as balloon angioplasty. It is possible that some portions of the underperfused region will contain non-viable cells for which improved blood supply will not affect the cell status. The underperfused region is preferably identified in lateral surface dimensions, and to the extent possible, in sectional dimension, to produce a lateral or volumetric image of the underperfused regions.

The source of oxygenated blood will typically be the arterial supply of blood localized in the pericardial, epicardial and outer myocardial layers of the heart, adjacent the underperfused region. Ideally, the source will be one in which an area of dense arteries less than about 1 mm branch into surrounding arterioles, and in which the arterioles with inner-lumen diameters between about 50–200 microns are plentiful. FIGS. 2A and 2B illustrate an artery 48 branching into arterioles 50 that form a suitable source of oxygenated blood.

In another embodiment of the invention, discussed below, the source of oxygenated blood is the interior of a ventricle chamber, where the method is practiced in a manner to promote blood supply between the interior of the chamber, across the endocardium, to the myocardial layer.

The oxygenated blood supply that is identified is proximate to a boundary or boundary portion 56 (FIG. 2A) of the underperfused region. This boundary represents the initial portion of the underperfused region which will receive increased blood supply as a vascular network from the blood supply to the underperfused region is formed. In the drawing, the boundary represents the 20–40% of the total underperfused region that is closest to the identified supply of oxygenated blood. Although more of the region may be included in the boundary, there may be little gain in increased vascularization of the underperfused region, until the boundary region itself can be initially vascularized, assuring sufficient blood cells in reserve for later new growth distribution. Thus, the method may involve an initial treatment to vascularize the boundary of the underperfused region, and subsequently using the new vascular supply as the source of oxygenated blood for extending the vascular network deeper into the underperfused region, that is, into the region below the initial boundary portion shown in FIG. 2A.

The area between the identified source of oxygenated blood and the underperfused region, including the boundary portion of the underperfused region, and the tissue expanse 58 between the underperfused region and the source of oxygenated blood, is identified from the imaging step as a target area 60 (typically a volumetric region) at which the stimulus for angiogenesis is to be introduced, as will be described. Within this target area, the user will identify a plurality of sites, such as indicated at 62, at which a stimulus will be applied. The sites in the target area have a preferred site-to-site spacing of between about 0.5 to 1 cm.

A variety of tools are available for imaging the heart, and localizing regions of subnormal blood circulation. One such tool involves monitoring blood flow in the heart by myocardial perfusion imaging (MPI) by single-photon emission computed tomography (SPECT) positron-emission tomography (PET), echoplanar imaging or angiography. These techniques are described in the literature (e.g., Amanullah, Mannting, Golub, Hansen, Toma, Dietlein, Sand, Marwick, Yang, Inuoe, and Nishimura).

Alternatively, or in addition, the patient's heart can be imaged by magnetic resonance imaging (MRI), including myocardial perfusion imaging by dynamic contrast MRI. Pertinent methods have been detailed in the literature (e.g., Furber, Lauerma, and Sechtem). Thallium scintigraphy is yet another imaging method technique available (e.g., Machecourt).

In addition an assessment is made to determine the pre-existing level of tissue demand for oxygenated blood. The heart has naturally occurring angiogenesis when disease progression occurs slowly so the high stress/exercise demand periods requiring blood flow do not exceed the compromised supply. By way of example a Class 4 Angina (measure of chest pain and class 4 is usually indicative of near constant pain) would be a good indicator of high level demand for new capillary growth. When high grade angina is not present patients will typically receive an exercise or chemical stress test where cardiac reserve can be quantified. Physicians may also use their own predictive skills when finding a high grade, non-symptomatic untreatable distal coronary artery blockage. When high grade demand is not present it can be added by using a biologic trigger as described herein. When general health permits demand can be increased with exercise.

Once the target-area and sites within this area have been identified, a stimulus effective to stimulate angiogenesis in the myocardial tissue from the source of the oxygenated blood to the underperfused region is introduced at each of the target sites. As will be discussed in detail below, the stimulus may be an angiogenic growth factor that is introduced either as a growth-factor protein, a vector capable of transfecting myocardial cells, to produce the desired protein growth factor, or cells which have been transfected in vitro to contain the desired growth factor. Alternatively, the stimulus may be a biological trigger, such as a tissue. injury produced by a mechanical, laser, electrical, radio frequency, chemical, thermal, or ultrasonic injury. The stimuli introduced may be in the form of a combination of growth factor and injury.

Figure 3A:
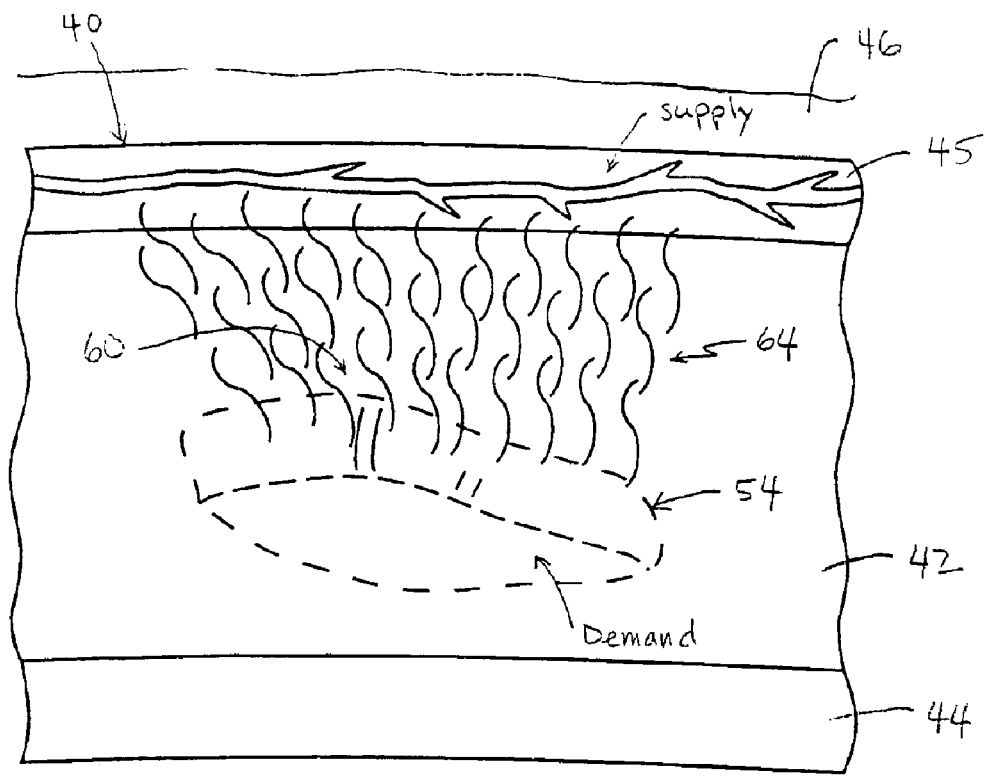
FIGS. 3A and 3B illustrate the development of capillary blush in an underperfused region of a heart ventricle wall (3A) and subsequent development of arterioles with sustained demand (3B), where the source of blood supply is a coronary arterial supply.
Figure 3B:
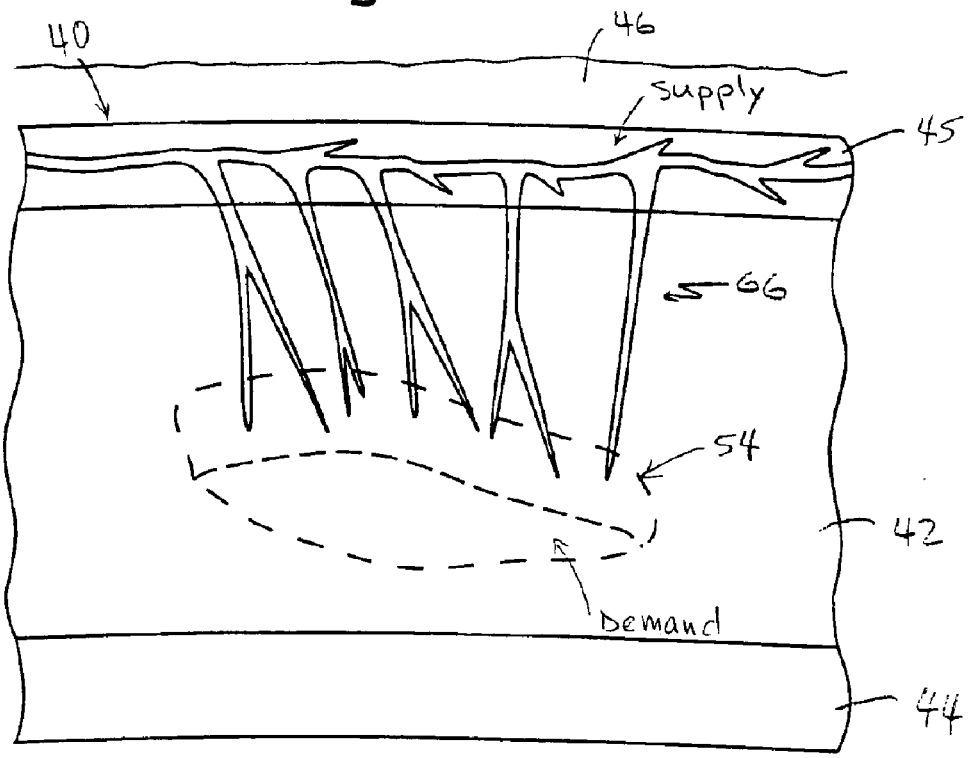

FIGS. 3A and 3B illustrate the supply/demand model of vascularization on which the present method is based. The model has four components: (i) a supply or source of oxygenated blood; (ii) a localized underperfused region which represents a demand for increased oxygenation, (iii) localized stimuli applied to a target area between the source of blood and underperfused region, to induce a capillary blush in the target area, and (iv) a sustained demand for oxygen in the underperfused region which is effective to convert the capillary blush to a stable and effective arteriole vasculature supplying the underperfused region from the source of oxygenated blood.

The initial angiogenic event is a capillary blush, such as indicated at 64 in FIG. 3A. This blush is made up of a fine network of capillaries, and typically is formed within 3–15 days after the initial angiogenic stimulus. The formation of the initial capillary blush requires a poor supply of oxygenated blood, and an angiogenic stimulus, but not necessarily a demand for increased vascularization. Without a sustained demand, or without a continuous introduction of stimulus, the capillary blush will begin to fade within several weeks, and eventually the heart will return to its pre-treatment conditions.

In accordance with the invention, an effective, and long-term vascular network from the source of oxygenated blood to the underperfused region is created by maintaining a sustained oxygen demand (or creating conditions of a natural sustained demand), until the capillary blush matures into a network of arterioles, such as indicated at 66 in FIG. 3B, which are supplied by the source of oxygenated blood, and which extend into the target area, to supply oxygenated blood to the previously underperfused region.

Thus, the treatment method has three key features: (i) the identification of a target site between an area of oxygenated blood supply and an underperfused region, (ii) the introduction of angiogenic stimuli in this area, to create a capillary blush in the area, and (iii) conditions of a sustained demand, produced either naturally or artificially, that cause the capillary blush to develop into a mature vasculature between the areas of supply and demand.

B. Stimulating Angiogenesis by Growth Factor

In one general embodiment of the invention, the stimulus introduced into the target-area sites is a growth factor effective to induce angiogenesis in the myocardial sites where it is introduced, including area surrounding the sites. Exemplary growth factors include basic and acidic fibroblast growth factor (FGF-2 and FGF-1, respectively), vascular endothelial growth factor (VEGF), platelet-derived growth factor (PDGF), insulin-like growth factor-1 (IGF-1), angiopoietin-1, angiopoietin-2, and combinations of two or more of these growth factors, including as angiopoietin-1 in combination with VEGF. Typical growth-factor doses, such as those given for VEGF (Murayama) or FGF-2 (Hasegawa), can be found in the literature. The growth factor introduced may be in the form of (a) a protein, typically made by recombinant methods, (b) a vector containing the coding region for the growth factor under the control of suitable human regulatory elements, or (c) myocardial cells which have been transfected in vitro to express the selected growth factor. Alternatively, the growth factor may be introduced through special cells, such as bonemarrow-derived endothelial progenitor cells (EPCs), that may contribute to neovascularization, introduced either alone or in combination with growth factors, such as VEGF, known to mobilize EPCs.

The growth factor may be introduced by a variety of means including (i) injecting the protein, vector, or transformed myocardial cells directly into myocardial tissue at each target-area site, (ii) drawing the protein or vector into myocardial tissue at each site by iontophoresis from a reservoir placed against the site, (iii) forming a channel in the myocardium at each site, and placing the protein, vector or cells into the channel, and (iv) bombarding each site with a biolistic particle containing or coated with the protein, vector or cells.

Methods for injecting pharmaceutical agents into myocardial tissue are known in the art, e.g., as detailed U.S. Pat. Nos. 5,685,853 and 5,661,133. One preferred device is the drug-delivery module disclosed in U.S. patent application Ser. No. 09/080,892, filed Sep. 24, 1998, which is incorporated herein by reference. Briefly, this device allows successive regulated introduction of a metered amount of a drug agent into a cardiac site, for example, as an attachment to an endoscope. The drug-delivery device may also be equipped with a sensing device, such as the ultrasound device disclosed in U.S. patent application Ser. No. 08/852,977, filed May 7, 1997, also incorporated herein by reference, which provides the user with information about the distance of the injection head from the surface of the heart.

Ionotophoretic administration of a growth factor protein or vector may be carried out by placing embedding the protein in a porous electrode, placing the electrode against the pericardial wall corresponding to one of the target sites, and applying a current across the electrode. The counter-electrode may be any attached to any external site on the patient.

A variety of tools are available for forming transmyocardial channels, e.g., by laser ablation, ultrasound, mechanical means, or the like, and these tools may be combined with suitable delivery tools for introducing into the channels, the selected protein, vector, or transformed cells. One suitable drug delivery device that employs laser ablation for drug delivery is disclosed in U.S. Pat. No. 5,925,012, which is incorporated herein by reference.

For biolistic introduction of growth-factor protein, vectors or transformed cells are known, the agent to be delivered is introduced into a high-pressure stream of fluid, e.g., air or water, and directed against the pericardial surface of the heart. Alternatively, the device may be designed to puncture the pericardium, and introduce the material in a high-pressure stream directly into the myocardial layer.

Methods for producing human growth factors are known, e.g., by recombinant production are known, as are vectors suitable for transforming human cells to achieve expression of selected growth factors (refs). Myocardial cells transformed in vitro with angiogenic growth factors, and injected into myocardial tissue have also been reported (refs).

The growth factor may be introduced in free, that is, solution or suspension form, encapsulated within suitable carriers, such as liposomes or biodegradable particles. Gold particles suitable for biolistics are well known, as are methods for introducing projectile particles into tissue (refs).

Figure 4A:
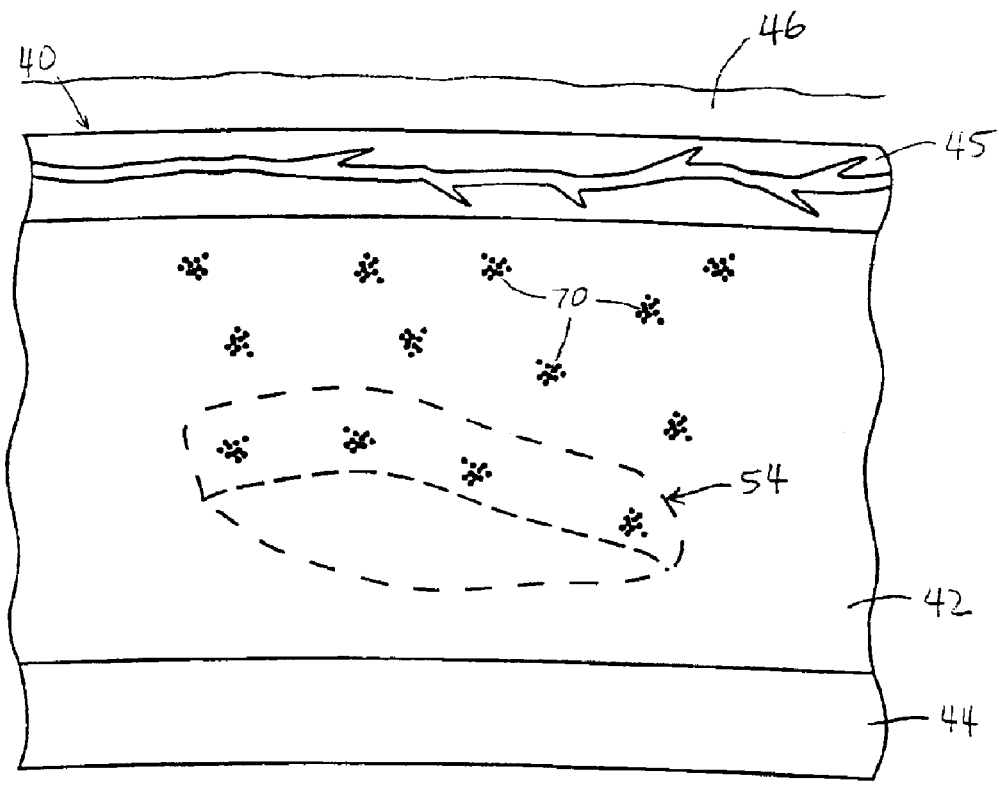
FIGS. 4A and 4B illustrate the distribution of growth-factor stimulus introduced in a target area of an underperfused region of a heart for achieving substantially uniform distribution of a growth factor (4A), and for achieving a higher short-term growth factor effect close to the blood supply, and a longer-term growth-factor effect close to the underperfused region.

The introducing step may be carried out in a manner that achieves a desired spatial or temporal pattern of growth factors at the target-area sites. The pattern shown in FIG. 4A is a uniform spatial and temporal pattern in which the growth factor is equally accessible at roughly equal concentrations at each site, such as site 70, where the drug in free form is represented by dots in the figure, and the sectional view is like that in FIGS. 2A, 3A and 3B, where similar numbers represent similar anatomical features. With this pattern, substantially each site with the target area is exposed over the same time period to the same to the same concentration of growth factor. This pattern of growth factor results in a capillary blush that has a relatively short duration, e.g., a period of a few weeks, without a sustained demand for oxygen at the underperfused region.

Figure 4B:
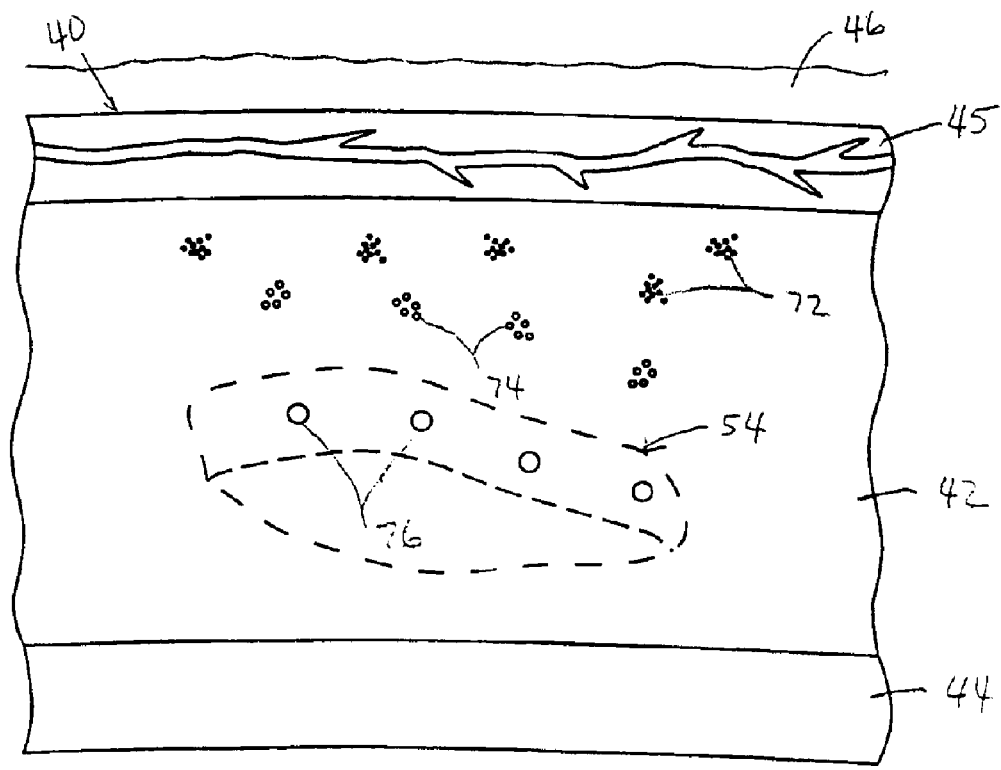

The pattern of growth factor shown in FIG. 4B is designed to produce a temporal gradient of angiogenic factor that produces a relatively high, short-term concentration of the agent closest to the oxygen supply, where capillary blush is initiated, and a longer-term release of growth factor progressing toward the underperfused region. The temporal gradient is produced by introducing into the sites closest to the blood supply, such as sites 72, a freely usable form of growth factor, e.g., the growth factor protein in solution form. At sites intermediate the blood supply and underperfused region, such as sites 74, the growth factor is packaged in a controlled release form, such as in a biodegradable particle, or in a form of a transforming vector, that functions to meter growth factor from the site over a relatively long period, e.g., 1–4 weeks. At sites close to or within the boundary of the underperfused region, such as indicated at 76, the growth factor is contained in an even slower-release form, e.g., for growth-factor release or production for a 1–3 month period of longer. This temporal distribution of growth factor allows for initial formation of capillary blush near the source of oxygenated blood supply, followed by angiogenesis at progressively deeper levels in the myocardium.

C. Stimulating Angiogenesis by Injury

In another general embodiment of the treatment method, the angiogenic stimulus is provided by a biologic trigger, an injury to the myocardial tissue, either alone or in combination with an angiogenic growth factor. Heart-muscle injury is known to produce a sequence of biochemical responses that ultimately lead to angiogenesis. This sequence generally involves a hypoxic condition following injury, leading to build up of lactic acid in the injured area, which stimulates macrophage infiltration into the injury site, stimulation of angiogenic factors by the macrophages and, in response to the growth factors, epithelial cell proliferation leading to capillary formation.

One feature of injury as an angiogenic stimulus is that the injury may also contribute to the sustained demand for oxygen necessary for stable vasculature development in the target area and underperfused region. That is, until the injury is resolved, the body will attempt to supply the injury area with increased blood supply as part of the response to injury. The ideal injury is a recurrent injury, and/or one slow to resolve, but at the same time, is resolved with a minimum of scarring, which is the body's way of resolving an area of cells destroyed by the injury and where the degree of surrounding inflammatory and angiogenic effect is maximized or compliments the co-delivered angiogenic compound. For example a more thermal injury is slower healing and might compliment a time release gell-based angiogenic drug co-placement, while a more abrasive/inflammatory injury might compliment a short lived gene or protein construct.

Figure 5A:
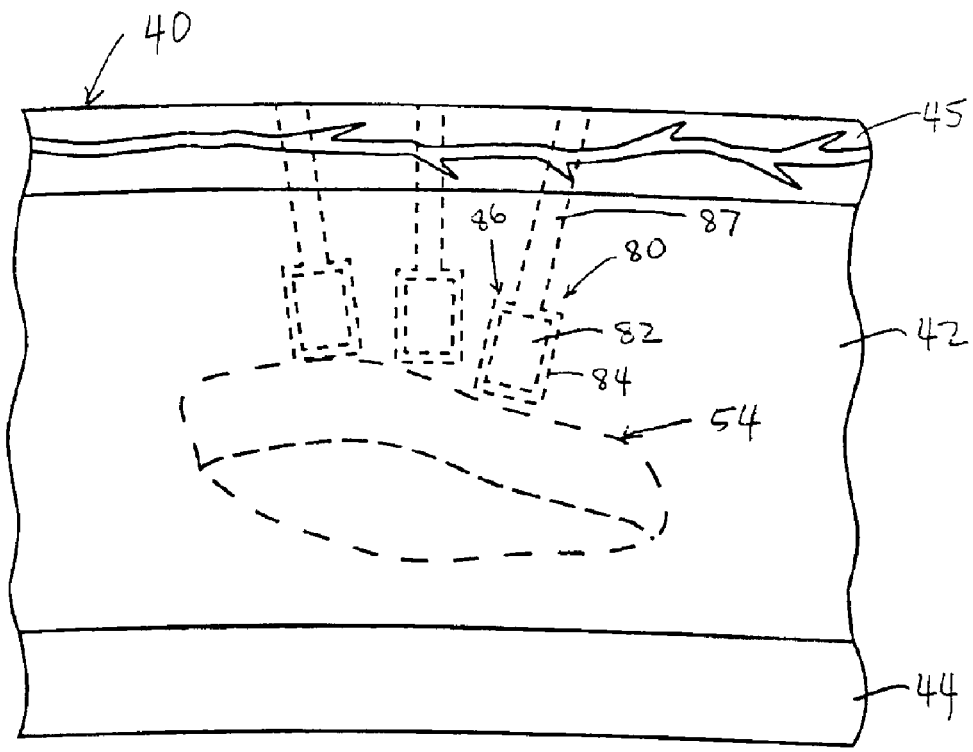
FIGS. 5A–5D illustrate various methods of producing an injury stimulus to a target-area of adjacent an underperfused heart region, including a mechanical to "coring" injury (5A), a mechanical wire injury (5B), a laser-induced channel injury (5C), and a combination of a mechanical wire injury and growth factor stimuli.

FIGS. 5A–5D illustrates several types of injuries suitable as angiogenic stimuli in the present invention. In each of these cross-sectional figures, anatomical features corresponding to those described in FIGS. 2A, 3A and 3B have the same figure numbers as in those figures. The injury illustrated in FIG. 5A is a novel coring injury, such as injury 80, that results in a core or island 82 of healthy cells surrounded by an annulus 84 of injured cells at each target-area site, such as site 86. The injury is made in a way that leaves a relatively narrow channel injury 87, in the epicardium, about 2–3 mm in depth, and the annular injury about 2–3 mm in depth in the myocardial layer, at the target site 86. The core injury minimizes the total amount of destroyed cells in the myocardium, while leaving a large injury area that will become vascularized, both within and outside the core, and an injury that may be relatively slow to resolve. The coring injury can also be made from the ventricle starting at the endocardium. Additional details of a coring device used to produce such an injury and its method of use are given in Section II below.

Figure 5B:
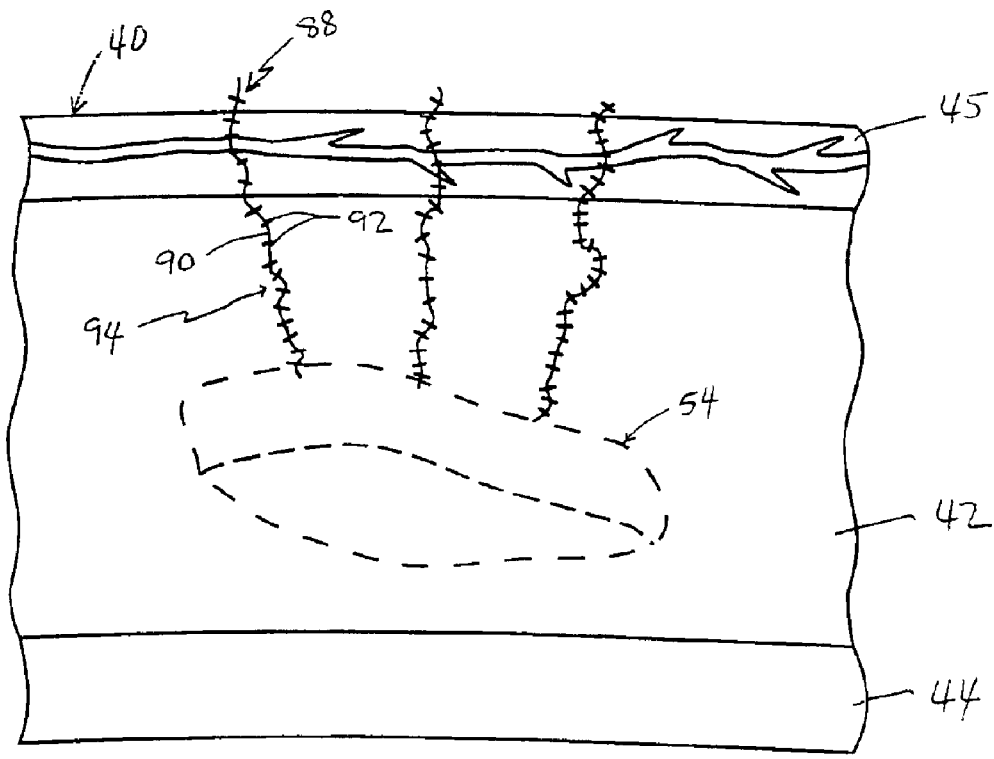

FIG. 5B illustrates a mechanical injury produced by a wire device, such as device 88. The wire device, which is described in greater detail in Section III below, includes a wire 90 having a series of barbs or cutters, such as barbs 92, along its length. Although not shown here, the device may have a proximal-end thread by which the device can be can be extracted from a remote, e.g., external body site. To produce the initial angiogenic stimuli, a wire device is inserted at each preselected target-area site 94 in the heart. As the heart tissue attempt to resolve the injury, an initial capillary blush develops in the target area. At periodic intervals after wire placement at the sites, e.g., typically at intervals of hours or days with longer intervals possible using smaller devices and anti-fibrotic coatings, the wire may be partially extracted, preferably from a remote site, as discussed in Section III. This pulling drags the wire barbs through the initial injury site, producing a recurrent injury that sustains the demand for oxygen within the target site, and thus promotes transformation of an initial capillary blush into a more stable arteriolar blood supply to the underperfused region. Over a period of several weeks or months, the wire devices will have been completely extracted from the heart, and are thereafter removed from the patients' body.

Figure 5C:
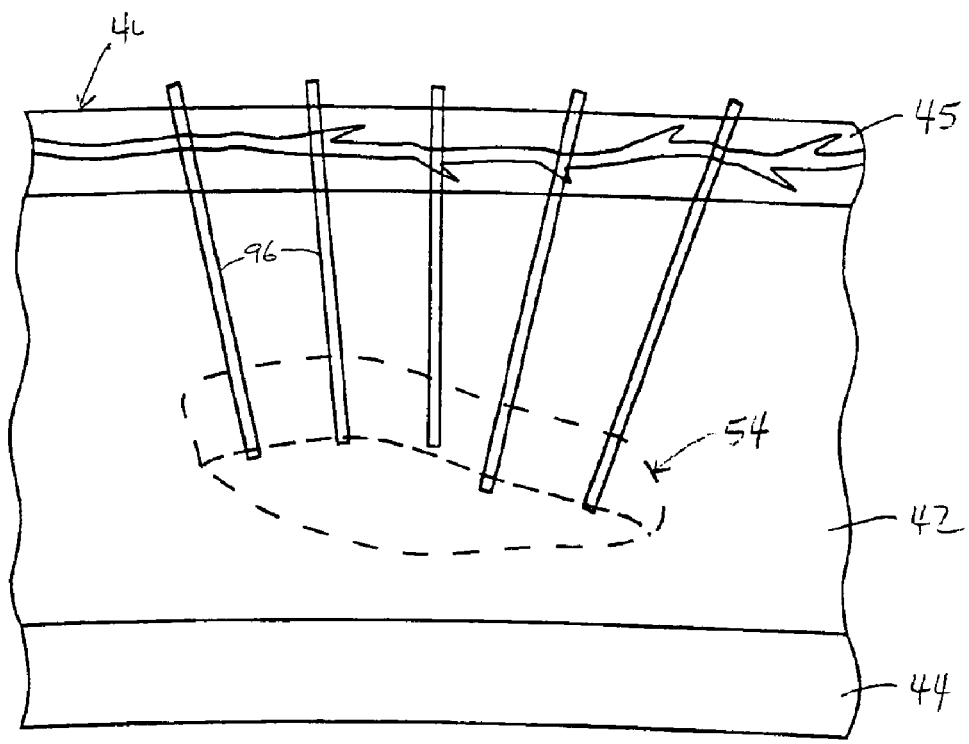

FIG. 5C illustrates an injury produced by an energy beam source, such as a laser beam. As illustrated, the beam produces channels, such as channels 96, of vaporized or otherwise destroyed cells that extend through the epicardium into the myocardium, and form the angiogenic sites in the target area. The channel thickness, which is larger than the laser-beam width, is typically about 1 mm; the channel depth ranges typically between about 4–8 mm, and extends either into or through the myocardial layer. Over time, the channel fills with clotted blood and it is ultimately resolved by vascularization in the target area, and scar formation in the channel areas. Apparatus for producing laser-channel injury to the heart, in a procedure known as transmyocardial revascularization (TMR) is described for example, in U.S. Pat. Nos. 5,931,834 and 5,785,702. The present invention differs from known TMR methods in that the injury channels are placed selectively in a target-area preselected to bridge the region of myocardium between a supply of oxygenated blood and an underperfused region. This has the advantage over the prior art of maximizing the vascularization effect of the channels, while minimizing the number of channels, and thus extent of scarring injury to the heart needed to effectively revascularize an underperfused heart region.

Figure 5D:
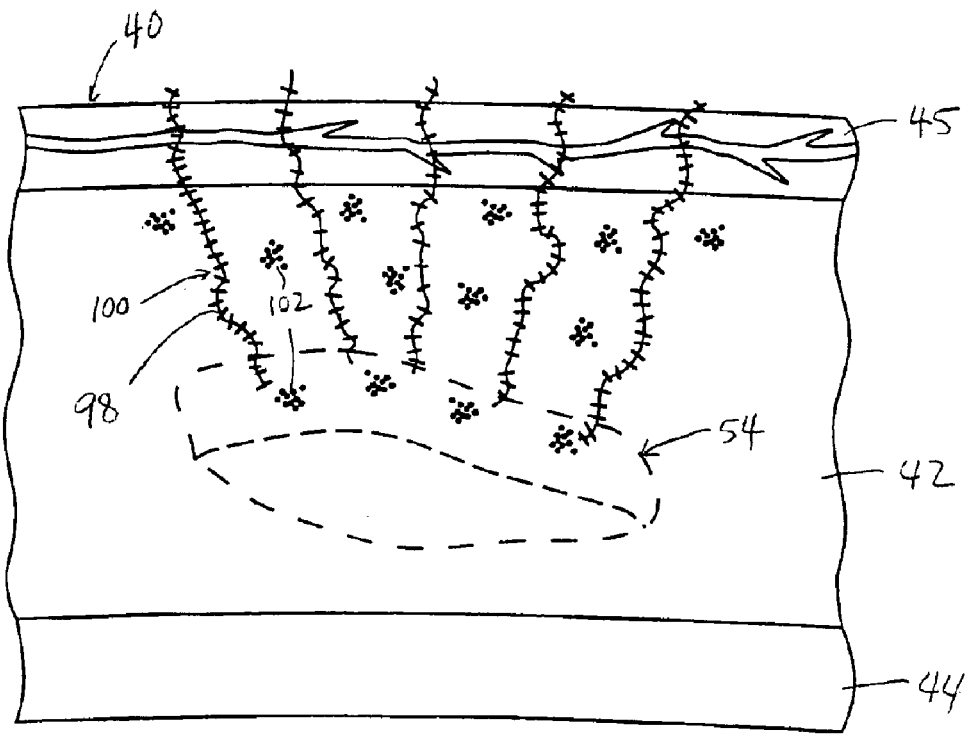

In each of the injury methods outlined above, the injury can be combined with added growth-factor stimuli to augment or accelerate the development of the original capillary blush, or to augment the development of a mature vasculature in the target area. For example, in the channel injury illustrated in FIG. 5C, an angiogenic growth factor may be introduced into the channels, or introduced into separate sites in the target area. A combined injury/growth-factor stimuli is illustrated in FIG. 5D, which shows a target area having injury stimuli produced by wire devices, such as device 98 at preselected target-area sites, such as site 100, and sites of growth-factor placernent, such as site 102. The growth factors assist initial capillary blush, and the wire devices are manipulated, as above, to produce a recurrent-injury demand on the developing vasculature.

In a second general embodiment, the source of oxygenated blood flow for supplying an underperfused myocardial region is the interior of the hearts left or right ventricle walls. Normally, blood passing from the interior ventricle chambers into the myocardium supplies only about 20% of the oxygen needs of the heart, the other 80% being supplied coronary arteries surrounding the outside of the heart. In subjects having adequate oxygen supply to the heart muscles, the relatively non-porous endocardium, which limits blood flow from the ventricle chambers into the myocardium serves to hold blood dampen extremes of pressure occurring in the ventricles. However, in subjects with underperfused regions of myocardium, it would be useful to make localized wall regions of the ventricle more porous, to allow direct blood supply from the ventricle interior to the adjacent undersupplied myocardium.

Figure 6A:
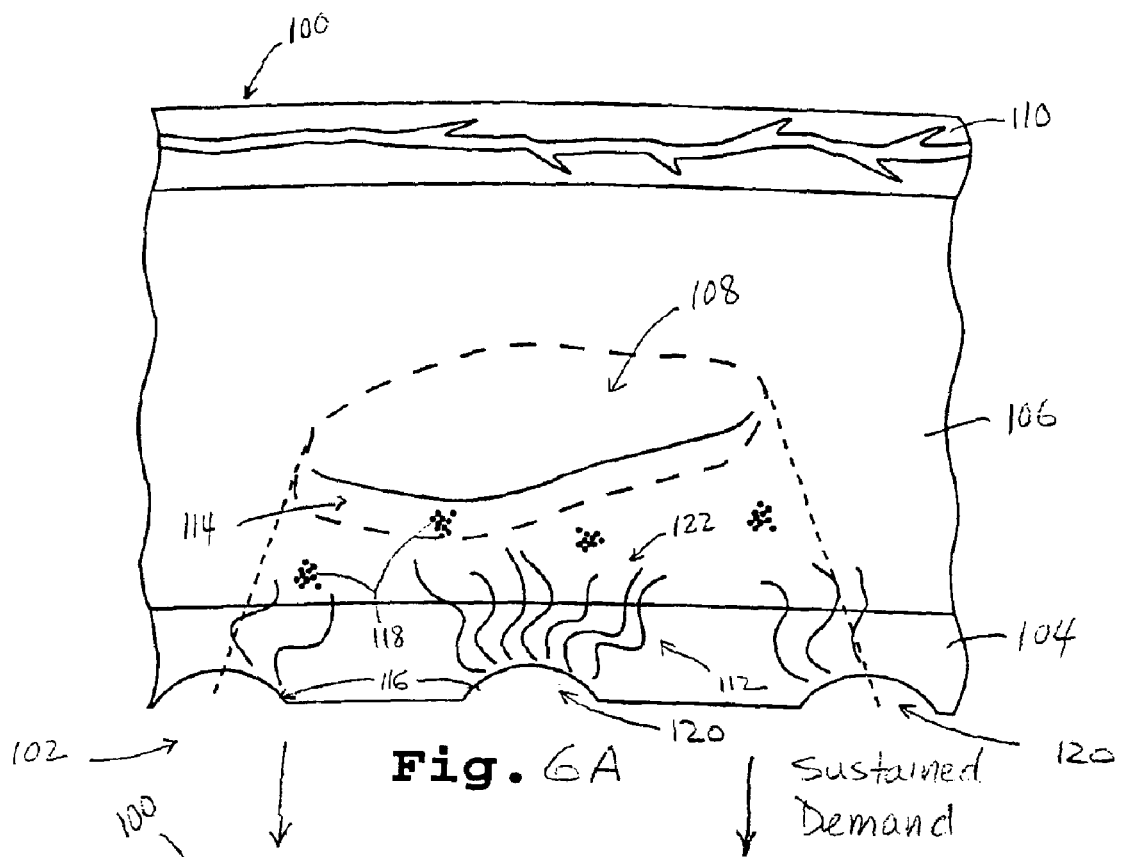
FIGS. 6A and 6B illustrate the development of capillary blush in an underperfused region of a heart ventricle wall (6A) and subsequent development of arterioles that occurs with sustained demand (6B); where the source of blood supply is the interior chamber of the heart left ventricle.
Figure 6B:
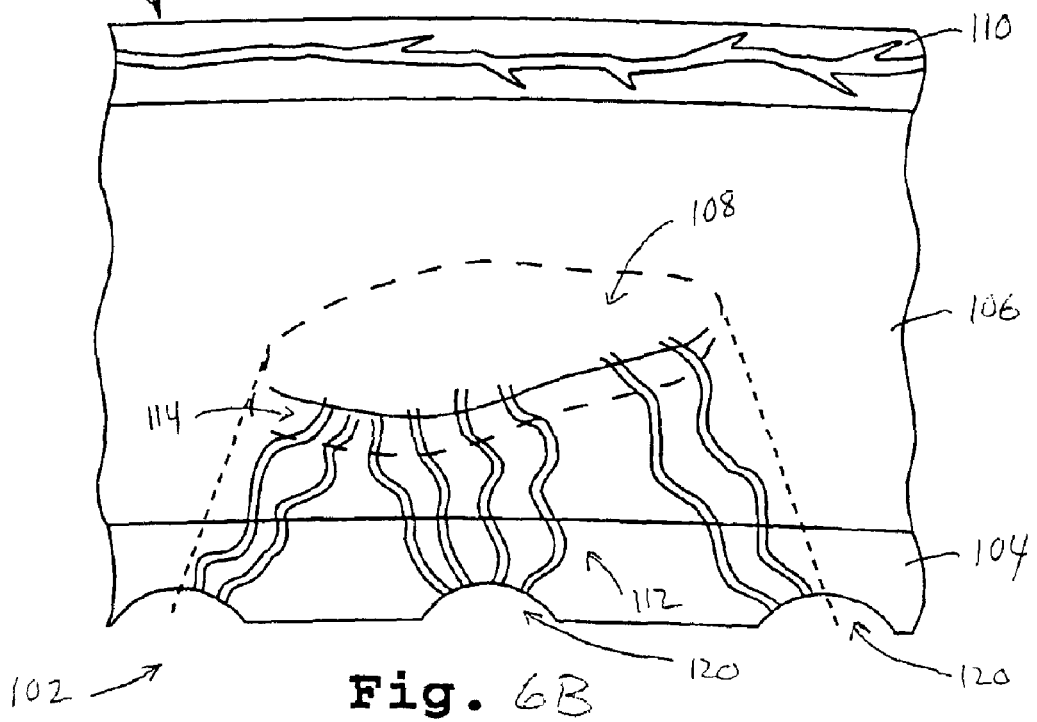

This is done, in accordance with this general embodiment, by using a biological trigger to produce an injury to the ventricle wall, adjacent the underperfused regions and/or by introducing growth factors at sites in a target area located between the underperfused regions and immediately "underlying" endocardium. The method is illustrated in FIGS. 6A and 6B which show a crosssectional ventricle portion 100 of a heart, including a ventricle chamber 102, an inner endocardial layer 104, a myocardial layer 106 containing an underperfused region, 108, and an outer epicardial layer. The target area in the method is a region 112 between the inner wall of the ventricle chamber and the underperfused region, and includes a boundary 114 in the underperfused region adjacent the ventricle wall. In practicing the method, one identifies (i) target area by imaging, as above, and (ii) a plurality of target-area sites for introducing an angiogenic stimulus. The sites may be sites such as sites 116, on the inner ventricle wall, when the angiogenic stimulus is an injury to the inner wall, and/or sites, such as sites 118, within the ventride wall, when the angiogenic stimulus is a growth factor. The growth factor is introduced at the preselected sites by one of the methods outlined above. The injury to the inner ventricle wall is preferably produced by a skiving or channeling tool, which produces elongate channels, such as channel 120 along the inner ventricle (endocardial) wall surface. The skiving tool and its application to the present method are detailed in Section III below.

FIG. 6A illustrates a network 122 of capillaries that make up the initial capillary blush in response to the injury and/or growth-factor stimuli. Over time, and with the continued stimulation provided by the channel injuries, this capillary blush will develop into a more stable blood-supply source to the underperfused region, either by forming more stable arterioles or through the maintenance of the oxygen demand by the injury.

The treatment method also contemplates treating an underperfused region of the heart by combining the treatment directed at the "outer" boundary of the region, as described with respect to FIGS. 2–5, with the treatment directed at the "inner" boundary of the heart, as described with respect to FIG. 6.

D. Sustaining Demand

As already noted, the treatment method requires continued demand for oxygen at the underperfused site to convert the initial capillary blush into a more stable and effective oxygen supply from the blood-supply source.

In one general embodiment, detailed in Section V below, the demand for oxygen is maintained by stressing the underperfused region by exercise. Briefly, the patient is equipped with an exercise monitor that indicates the level and amount of heart exercise the patient achieves. Typically, the patient should begin the exercise regimen within 3–8 days following the introduction of angiogenic stimuli to the heart. The patient is required to achieve a given exercise level for a period of at least 14 days, and preferably for a period of 2–3 months, following capillary blush formation. The amount and level of heart exercise is effective to stimulate the conversion of capillary blush produced by said step (b) to arterioles in the target area. The level can be readily derived from reviewing the result of a patients baseline exercise stress testing, and developing a heart rate level and time which is both safe and challenging. The exercise monitor can provide the safety and record keeping necessary. A pacemaker may be temporarily or permanently added to exercise the heart.

In another general embodiment, the sustained demand is produced by a slow-healing or recurrent biological trigger, such as outlined above, and also considered in detail in Sections II, III, and IV below. The demand for oxygenated blood created by the injury is sustained for a period of at least 2–3 months, following capillary blush formation.

II. Method and Device for Mechanical Coring Injury

FIGS. 7A–7B and 8A–8C illustrate various coring-injury-producing devices. These devices are designed to produce various types of coring injuries, such as an injury that defines a disk-shaped area or carves out a conical portion of injured cells at a target site surrounded by healthy cells. The core injury is preferably produced below the surface in the myocardial layer and in such a manner as to minimize the total number of destroyed cells in the myocardium, while leaving a relatively large injury area that will become vascularized and that may be relatively slow to resolve. Localization of such an injury requires a tool that has a means of entry into the tissue which is lower in trama than the introduction of the injury itself which is preferably produced about 1–4 mm below the epicardial region in the underlying myocardial region.

Figure 7A:
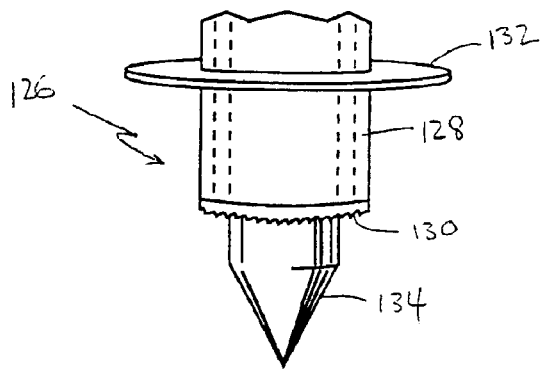
FIGS. 7A and 7B illustrate coring tools constructed in accordance with embodiments of the invention.

One such cutting tool that may be used to produce a subsurface coring injury is shown in its distal portion at 126 in FIG. 7A. The tool has an elongate sleeve 128 which can be guided to a selected heart target-area site, and which terminates at its distal end in a cutting surface 130. The sleeve carries a radially enlarged annulus 132 which limits the depth of penetration of the tool into the heart muscle.

Sleeve 128 accommodates a piercing element 134 which can be moved radially within the sleeve to project its piercing tip beyond the distal end of the sleeve. In operation, the piercing element is moved to such a position to function to pierce the epicardial layer when the tool is being introduced into the heart muscle, at a selected target-area site in the heart. Once the piercing tip has entered the myocardium, the sleeve may be advanced into the myocardium, with a cutting motion applied to the sleeve, to produce an annular cut through the myocardium tissue, typically about 2–3 mm into the myocardium.

To remove the tool from the heart, after the subsurface coring injury is made the sleeve is removed from the heart muscle, leaving a core injury of the type described in FIG. 5A above.

Figure 7B:
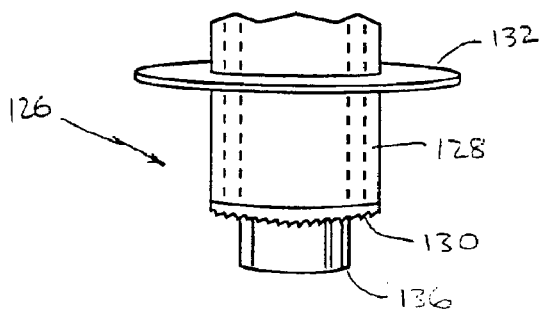

FIG. 7B shows a tool that can be used to make a surface coring injury. Here a blunt-end rod 136 is used instead of the piercing element 134. This rod is pushed against the tissue core inside the sleeve as the sleeve is being extracted, to hold the core in place during tool extraction. Other arrangements can also be used for holding the tissue core in place while the tool is extracted.

Figure 8A:
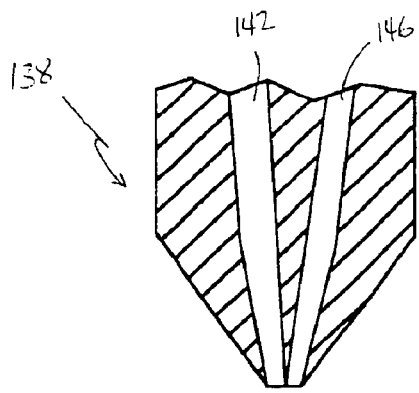
FIGS. 8A–8C illustrate various states of a coring/drug-delivery tool constructed in accordance with another embodiment of the invention.
Figure 8B:
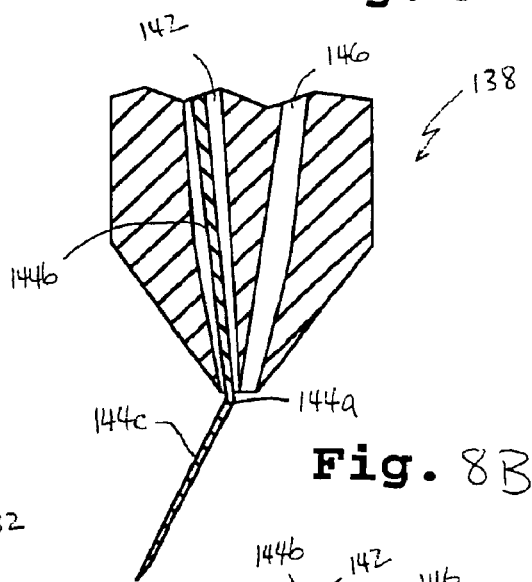
Figure 8C:
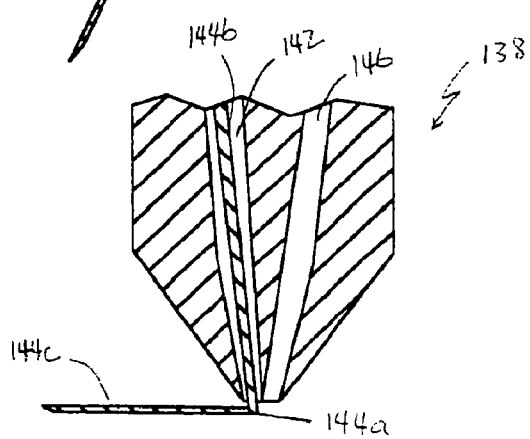

FIGS. 8A–8C illustrate the distal end portion of a coring and drug-delivery tool 138 constructed according to another embodiment of the invention. As seen, the tool includes a tipped needle having an axial bore 142 through which a blade 144 is received and a drug-delivery bore 146 through which a drug solution or suspension can be delivered from the needle. Blade 144 is an elongate, flexible metal blade that has a substantial bend at 144a adjacent its distal end, between a proximal guide segment 142b, and a distal cutting segment 144c.

In operation, the needle is introduced through the pericardium or endocardium into the myocardium at a selected target-area site where injury and optionally, growth factor is to be placed. During this introducing step, blade 144 is retracted into the bore of the needle. As the needle is being inserted a selected depth into the myocardial tissue, the blade is moved out of the needle bore. As the bend in the blade passes through the outer tip of the needle, the tension in the blade causes the distal segment of the blade to extend away from the axis of the needle, as illustrated in FIG. 8B, which shows a partial angle bend, and FIG. 8C, which shows a full right angle bend. The needle is then rotated to produce a conical section in the tissue defined by the distal blade's movement through a complete rotation.

Figure 9A:
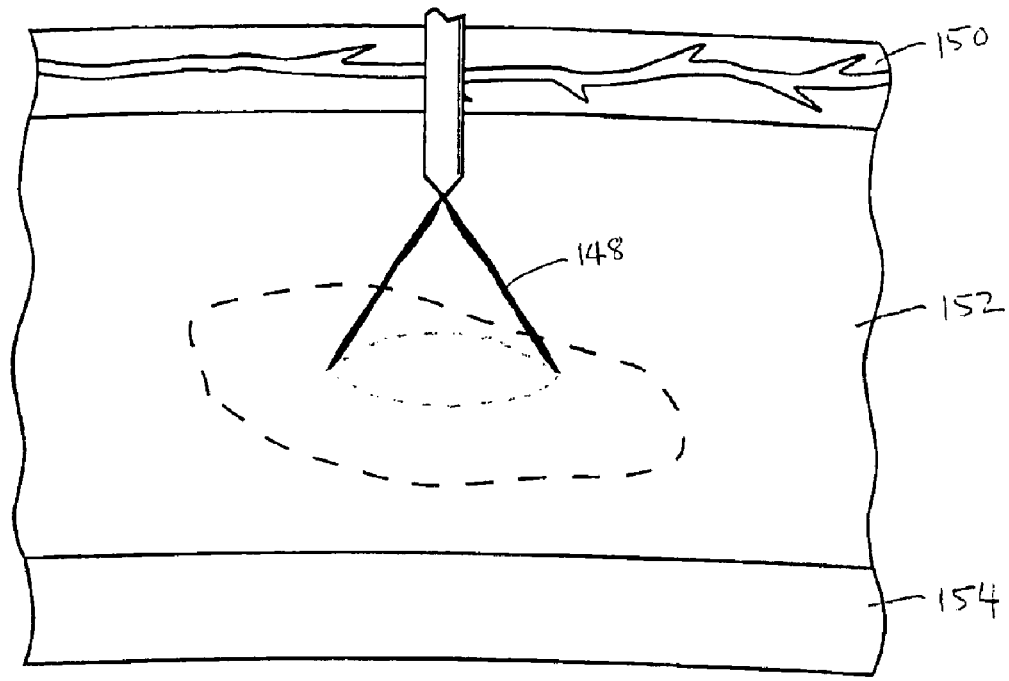
FIGS. 9A and 9B illustrate different types of myocardial-slice injuries producible by the coring/drug-delivery tool of FIGS. 8A–8C.

When the blade is partially extended as in FIG. 8B, such a rotation produces a conical core injury 148 such as shown in FIG. 9A, where the epicardial, myocardial, and endocardial layers are indicated at 150, 152, 154, respectively. After formation of the conical cut in the myocardial tissue, a growth factor solution of suspension may be introduced into the injury site under pressure through bore 146 in the needle. The separated tissue allows the drug agent to be received in bolus form at the site, where it distributes about the site of the injury and ultimately is absorbed into the cells adjacent the injury. In this way, a growth factor agent can be placed and distributed over a desired area within the myocardium.

Figure 9B:
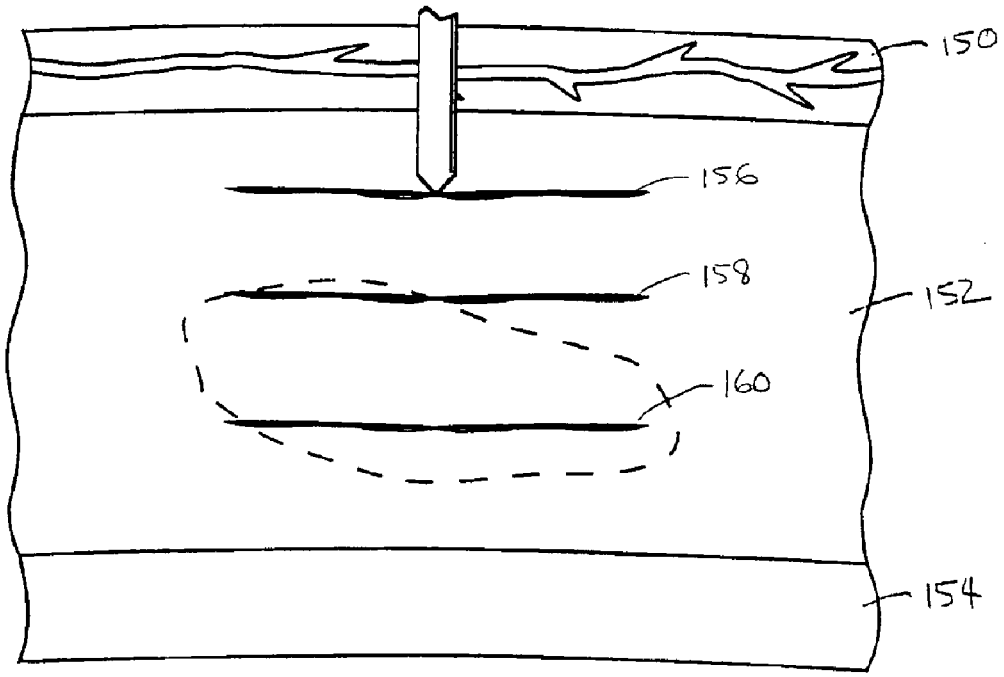

Likewise, when the cutting blade is extended passed its bend, and therefore assumes a full right angle in its cutting segment, as in FIG. 8C, rotation of the needle produces a substantially planar, circular cut such as indicated at 156, 158, and 160 in FIG. 9B. The three cuts in FIG. 9B were produces by making successively shallower circular cuts in the tissue, with retracting and extending the cutting blade at each new depth in the myocardium. At each circular cut, drug may be introduced, essentially filling the circular space cut into the tissue.

III. Method and Device for Sustained Wire Injury

Another device for generating an injury in accordance with the invention is illustrated in FIGS. 10–13. This device is adapted to be remotely activated at periodic intervals to produce recurrent mechanical or thermal injury at implantation sites throughout a target area over a total period sufficient to convert initial capillary blush induced at the implantation sites into arterioles.

One such device 156 comprises an elongate wire 158 formed with barbs, such as barbs 160, along its length. Device 156 preferably further includes a flexible thread 162, one end of which is attached to wire 158 and the other end of which engages an external hook 164.

Figure 10:
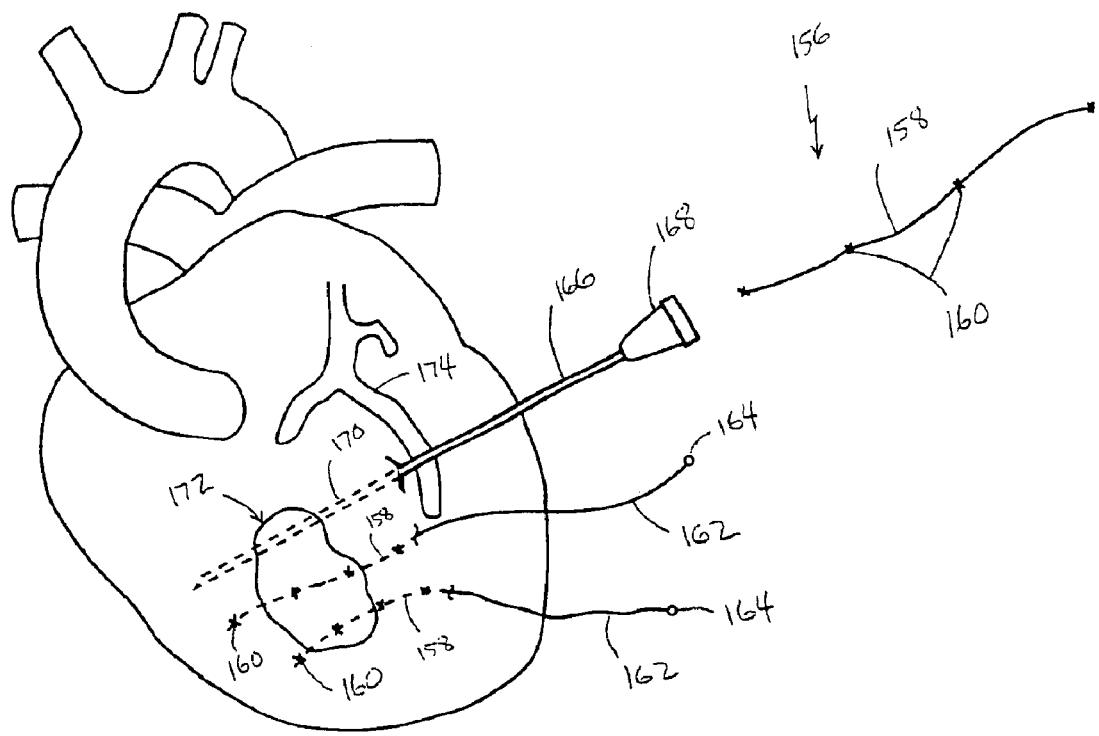
FIG. 10 illustrates how a wire tool is introduced into a target-area site in the heart, in accordance with one embodiment of the invention.

Placement of wire 158 is illustrated in FIG. 10. The wire may be inserted into the subject using a hollow needle 166 which includes a funnel-shaped guide 168 at its proximal end. The needle is inserted into the subject so that a portion 170 of the needle extends through a target area in the myocardium which includes an underperfused region 172, as shown in FIG. 10. The wire is then inserted into the hollow portion of the needle, such that when the needle is removed, the wire is implanted in the target area and extends through region 172 in close proximity to healthy tissue 174. Multiple wires may be inserted, as shown in FIG. 10.

Figure 11:
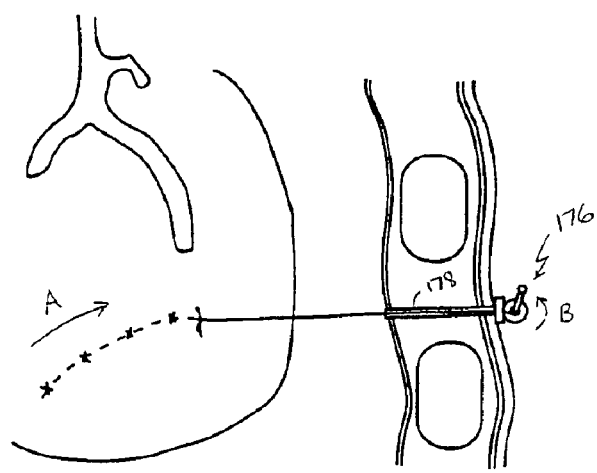
FIG. 11 shows how the wire tool can be controlled from an external chest site.

After insertion, each wire is periodically retracted a small amount, in accordance with the principles of the invention. A crank mechanism 176 in connection with a sleeve 178 that extends through the chest wall may be used to retract the wire, as shown in FIG. 11. Other suitable mechanisms may also be used.

Figure 12:
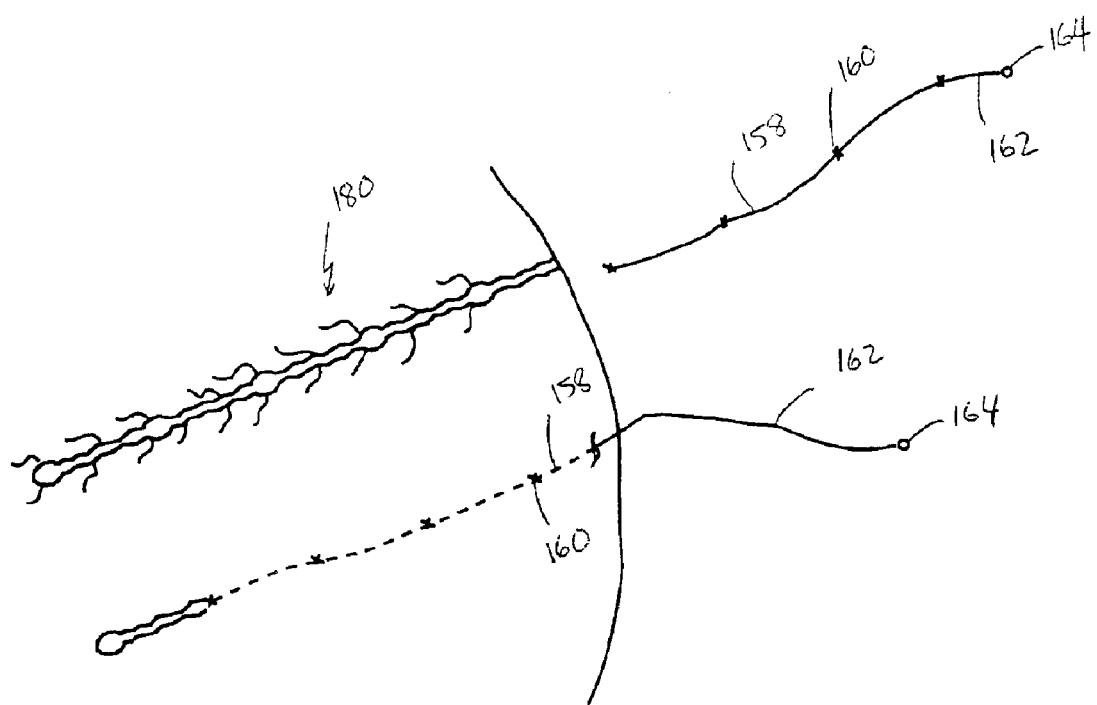
FIG. 12 illustrates the mechanics of vascularization that is produced by a sustained-injury from the FIG. 10 tool.

At periodic intervals of between 1–7 days, the wire is retracted an indexed amount of about 1 cm in the direction of arrow A by moving the crank handle in the direction of arrow B or otherwise pulling the wire to effect the retraction. These times and distances are exemplary only; the amount of removal and the periodic intervals at which the wire is incrementally removed will vary depending on the healing response curve desired. The result, as shown at 180 in FIG. 12, is that each indexed (e.g., 1 cm) retraction creates a new or fresh tearing injury that promotes angiogenesis.

Figure 13:
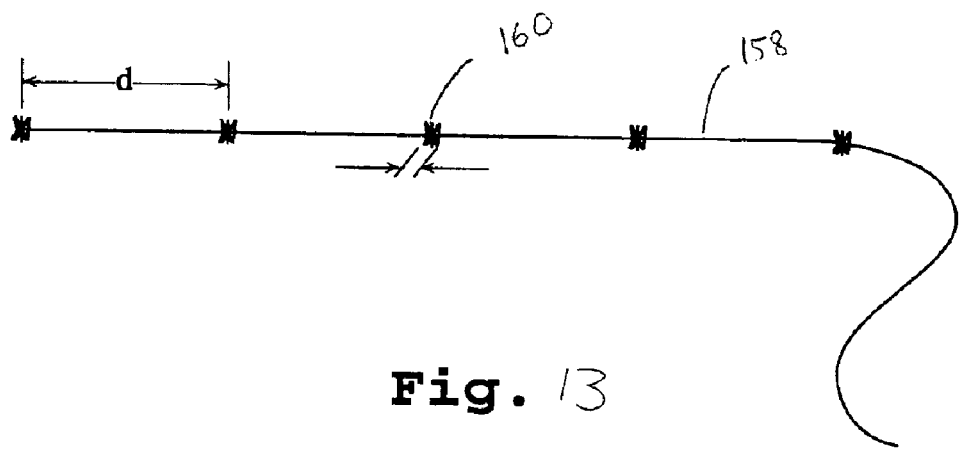
FIG. 13 shows details of a portion of the wire tool in FIG. 10.

The details of the construction of wire 158 are illustrated in FIG. 13. The wire is preferably between 0.002" to 0.005" stainless wire and formed of a bioerodable, ferromagnetic material. The wire preferably has 34 barbs spaced along its length approximately 1 cm apart, with the barbs themselves preferably being stainless and 0.010 type sharp bumps, although the number of barbs as well as their size and spacing will depend on the desired healing response.

In accordance with the principles of the invention, the wire is retracted in steps that are matched to a desired healing response curve. Periodic and discrete retraction of the wire along a predetermined track or path re-injures the tissue and results in a timed sequential injury that promotes arterioles to grow along the track in a more organized pattern, and thus concentrates blood flow along the track. The device may be shaped in other ways as well, including conduits for drug additions.

IV. Method and Device for Endocardial Injury

Figure 14:
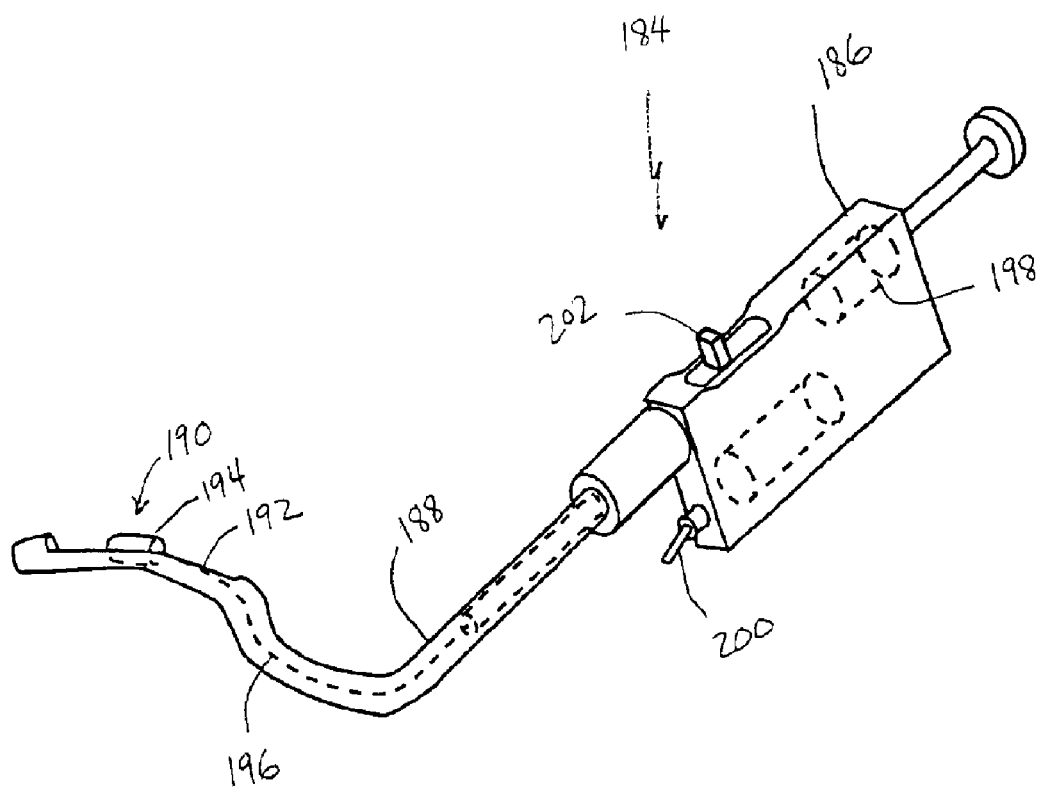
FIG. 14 is a perspective view of a cutting tool constructed according to one embodiment of the invention.

FIG. 14 illustrates one embodiment of a tool 184 for use in producing an injury at selected locations on the inner endocardial wall of a heart ventricle. As discussed above, the purpose of this injury is to stimulate angiogenesis that can supply blood from the ventricle chambers of the heart to underperfused regions in the ventricle wall.

Tool 184 generally includes a handle 186 by which the operator guides and operates the tool, an elongate, rigid handle extension 188, and a cutter element 190 formed at the distal end of the handle extension. The cutter element has a curved shape, as shown, allowing the element to be placed firmly against the curved wall portion of a ventricle chamber during operation, after (i) the cutter element is introduced through the heart muscle into the ventricle chamber, and (ii) the handle is manipulated to draw the cutter element against a ventricle wall surface.

The cutter element has a recessed segment 192 along which a cutter blade 194 is movable in guide tracks (not shown) under the influence of a cable 196 attached to the blade and a motor 198 housed in handle 186. Control of blade motion is through a switch 200 which activates the motor. A cutter retreat lever 202 is used to reset the blade to its distal cutting position.

Figure 15:
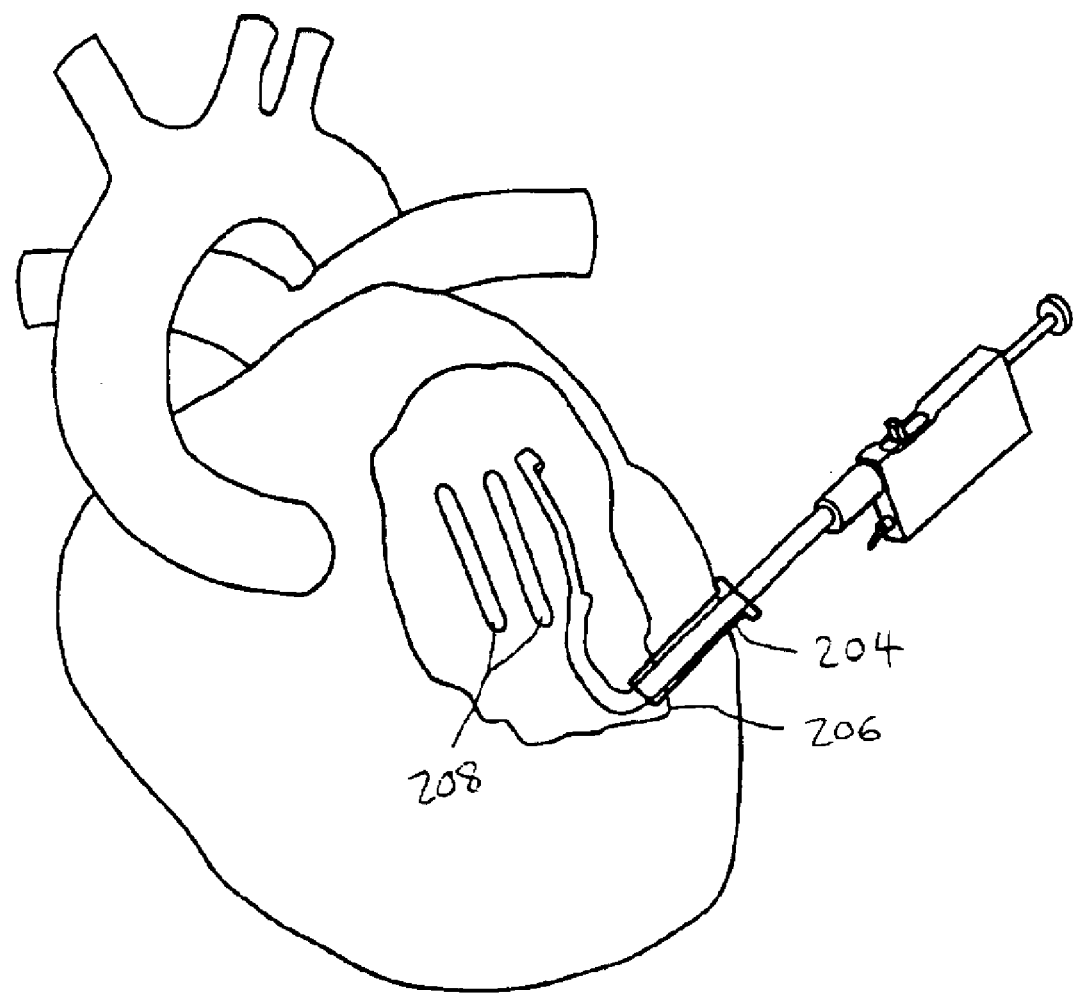
FIG. 15 illustrates the placement of the tool of FIG. 14 in producing a channel injury to a ventricle endocardial wall surface.

In operation, and with additional reference to FIG. 15, the tool is moved through a previously installed introducer sleeve 204 having a deformable seal that prevents blood flow from the ventricle chamber. The tool is placed inside the ventricle wall, indicated at 206, and placed against a wall region adjacent an underperfused region. The cutter blade is now activated to form a shallow channel injury 208 in the ventricle wall, as illustrated in FIG. 15. The tool is dimensioned to produce a channel of about 1–5 mm, preferably 2–3 mm in width and 0.52 mm, preferably about 1 mm, in depth. After each cut, the tool is moved to form an another cut in an adjacent target area, until the plurality of cuts corresponding to the region of the underperfused region are made. The channels are typically about 1–3 cm long, and spaced about 0.5 to 1 cm apart. apart. After the cutting operation, the tool is withdrawn, then the introducer sleeve is removed.

The tool may be adapted to produce a variety of ventricle-wall injuries, such as needle injury, coring injury, or laser injury by replacing the movable cutter blade with other injury-producing elements. For example, in the case of a needle injury, the cutter blade may be replaced by a movable needle housing through which a needle can be selectively extended, e.g., by a suitable control in the handle, at spaced intervals along the track of the cutter segment. Likewise, a coring element designed to produce a myocardial coring injury, such as detailed in Section III above, may be used. In addition, or alternatively, the tool may be equipped with a needle or biolistic element for introducing growth factor at selected sites in the selected target area between the ventricle wall and the underperfused region.

The injury andlor growth-factor stimuli introduced by the tool functions initially to stimulate angiogenesis in the region between the endocardial wall and the underperfused region, serving, in effect, to make the endocardium more porous to blood flow from the ventricle chamber to an adjacent region in need of more oxygen. The capillaries forming a capillary bed in response to the stimuli function as one-way blood-cell carriers, through the vaso-action motion of capillaries. Thus, the heart becomes leakier, but only in the desired endocardium-to-myocardium direction. With sustained injury, such as is produced by a channel injury or laser injury, the continued angiogenic stimulus leads to the formation of an arteriole or more robust capillary bed feeding the underperfused region from the ventricle wall. Alternatively, the initial stimulus can be followed by an exercise regimen, as described in Section V, to place a sustained demand on the growing vasculature.

This embodiment of the treatment method may be carried out in conjunction with other aspects of the invention that treat the underperfused region from the "epicardial" side of the underperfused region, or independently. An advantage of the combined methods is that the region in need of greater oxygen supply is revascularized from both sides of the heart wall. A second advantage is that the sustained demand placed on the region, such as by exercise, will contribute to vascularization being created on both inner and out sides of the underperfused region.

V. Method and Device for Sustained Stimulus by Exercise

In addition to long-term or recurrent injury, the oxygen demand within the underperfused region can be sustained by requiring the patient to achieve a desired level of exercise, as measured by an elevated heart rate, e.g., a 50–100% increase in heart rate over the resting rate, for a selected daily period, typically at least ½ hour. per day. The exercise regimen should begin at least by week 4 following the initial angiogenic stimuli, and be continued at least through week 15–16 following the initial stimuli. The desired end point is conversion of capillary blush to a more robust arteriole system, and the transformation of vasculature can be followed by imaging techniques noted above.

If desired, a pacemaker may be added to stimulate the heart at regular exercise intervals.

Figure 16:
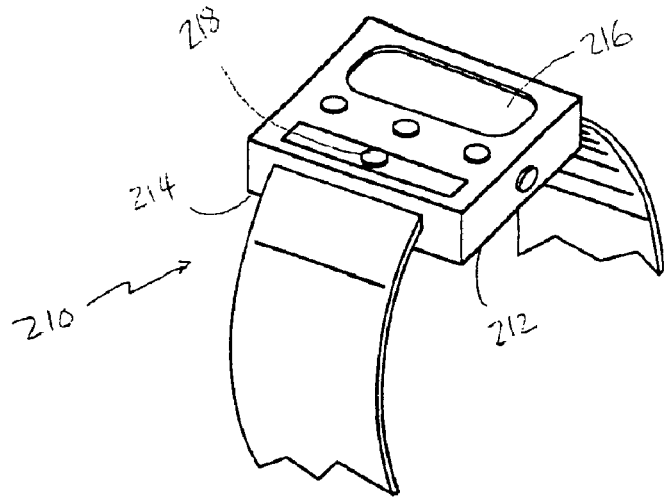
FIG. 16 shows an exercise monitoring device for use in monitoring and tracking heart-rate exercise, in creating a sustained demand to an underperfused region of the heart.

The monitoring and tracking components of the device are illustrated in FIG. 16. The device here takes the form of a wrist-worn device 210 having against-the-skin electrodes 212, 214, for detecting pulse rate. Other devices can be designed, for example to be strapped around the chest of the wearer, with against-the-skin electrodes being located at the chest region over the heart. The front face of the device includes a display window 216 and a switch 218 which sends an "activate" signal to the device, when the user initiates each daily exercise program.

Figure 17:
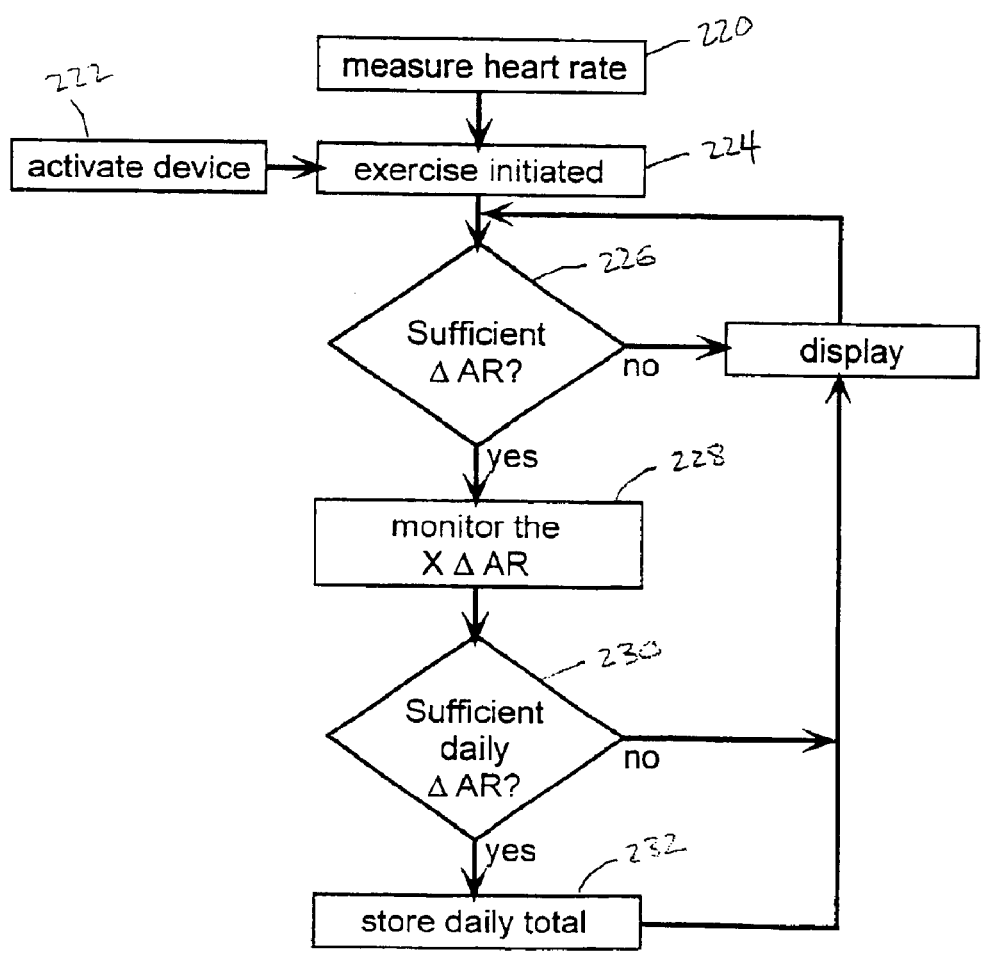
FIG. 17 illustrates the operation of the exercise-monitoring tool in FIG. 16.

The operation of the device is illustrated in FIG. 17, which is a flow diagram of the logic steps carried out by the device. Initially, when the device is strapped in place, the user allows the device to measure an average resting pulse, indicated by function 220, which provides a baseline of heart rate. By activating the device for exercise measurement, indicated by functions 222 and 224, the device is set to begin monitoring and timing the extent and duration of heart exercise over a given exercise period. The device monitors the heart rate and indicates to the user when an adequate rise in heart rate has been achieved, as indicated by function 226. Once the elevated heart-heart threshold is reached, the device begins measuring the duration of the period of elevated heart rate, indicated by function 228, and displays both heart rate and duration date to the user. When an integrated, elevated heart rate/duration threshold is reached, indicating a sufficient heart exercise for that day, the device so signals the user, as indicated by function 230. The daily exercise data is stored in a suitable storage device 232 that keeps track of the (i) days when heart-rate exercise was measured, (ii) the integrated elevated heart rate/duration value on each exercise day, and the total days remaining in the exercise regimen, and this data can be supplied to the user on demand, e.g., at the beginning of each daily exercise.

At the end of the exercise regimen, the user may be examined to confirm formation of arteriole blood supply to the underperfused region. Alternatively, the patient will be able to report improvement in vascularization of the heart through such measures as increased exercise tolerance, quality of life, or relief from cardiac insufficiency symptoms, such as resting or exercise-induced chest pain.

From the foregoing, it can be appreciated how various objects and features of the invention are met. In particular, the present invention addresses the problem: how can an underperfused region of the heart, and therefore a region at risk or infarct and muscle loss, be efficiently resupplied with an adequate supply of oxygen with a minimum of anatomical damage to the heart.

Although the prior-art recognized the ability of angiogenic stimuli, including both growth factors and injury, to stimulate angiogenesis in the heart, the present invention extends this solution in two key respects. First, by imaging the heart to identify and localize the underperfused region, and localizing this region with respect to the adjacent supply of oxygenated blood, the sites of angiogenic stimulus can be localized to optimally extend from the source of oxygenated blood toward the site of demand (the underperfused region). This significantly enhances of the efficiency of capillary blush formation. Secondly, by applying a sustained demand to the region where capillary blush has occurred, the initial capillary formation is assured of developing into a stable and robust vascular supply to the underperfused region.

It is claimed:

1. A method of inducing transformation of capillary blush into arterioles in a patient after a surgical procedure, comprising the steps of:
   (a) providing a monitor having a sensor for measuring the patient's heart rate, and a processor;
   (b) equipping the patient with the monitor;
   (c) using the sensor to measure the patient's resting heart rate;
   (d) elevating the patient's heart rate to a selected threshold by having the patient undergo exercise;
   (e) using the sensor to detect when the patient's heart rate has reached the selected threshold;
   (f) determining the duration of time that the patient's heart rate was above the selected threshold during exercise; and
   (g) using the processor to estimate an amount of time of exercise needed to induce transformation of capillary blush into arterioles based on the selected heart rate threshold and the duration of time determined in step (f).

2. The method of claim 1, wherein the monitor further comprises a display device, and wherein the method further comprises the step of displaying the duration of time determined in step (f).

3. The method of claim 2, wherein the method further comprises displaying the amount of time of exercise needed to reach a desired level of capillary blush into arterioles.

4. The method of claim 1, wherein the monitor further comprises a storage device, and wherein the method further comprises storing the resting heart rate measured in step (c).

5. The method of claim 4, wherein the method further comprises storing the duration of time determined in step (f).

6. The method of claim 1, wherein the monitor is configured to alert the patient that a selected heart rate threshold has been reached.

7. The method of claim 1, wherein the storage device maintains data on the dates upon which heart-rate exercise was measured, the integrated elevated heart rate/duration value of each exercise date, and the total dates remaining in an exercise regimen.

8. The method of claim 1, wherein the monitor is configured to send an signal to the patient to initiate an exercise program.

9. The method of claim 1, wherein the monitor is adapted to be strapped to the patient.

10. The method of claim 1, wherein the sensor comprises at least one electrode.

11. The method of claim 1, wherein the selected heart rate threshold is about 50 to about 100 percent of the patient's resting heart rate.

12. The method of claim 1, wherein exercise is performed on a daily basis, for at least about one-half hour per day.

13. The method of claim 12, wherein the exercise is performed on a daily basis for about 10 weeks.

14. The method of claim 1, wherein a pacemaker is utilize to stimulate the patient's heart.

* * * * *